(12) United States Patent
Kandel et al.

(10) Patent No.: US 8,848,186 B2
(45) Date of Patent: Sep. 30, 2014

(54) ANGLE-RESOLVED ANTISYMMETRIC SCATTEROMETRY

(75) Inventors: Daniel Kandel, Aseret (IL); Vladimir Levinski, Nazareth (IL); Noam Sapiens, Bat Yam (IL)

(73) Assignee: KLA-Tencor Corporation, Milpitas, CA (US)

( * ) Notice: Subject to any disclaimer, the term of this patent is extended or adjusted under 35 U.S.C. 154(b) by 124 days.

(21) Appl. No.: 13/386,524

(22) PCT Filed: Jul. 21, 2010

(86) PCT No.: PCT/US2010/042738
§ 371 (c)(1),
(2), (4) Date: Jan. 23, 2012

(87) PCT Pub. No.: WO2011/011511
PCT Pub. Date: Jan. 27, 2011

(65) Prior Publication Data
US 2012/0120396 A1 May 17, 2012

Related U.S. Application Data

(60) Provisional application No. 61/227,722, filed on Jul. 22, 2009.

(51) Int. Cl.
*G01B 11/00* (2006.01)
*G01J 4/00* (2006.01)
*G03F 7/20* (2006.01)
*G01B 11/24* (2006.01)
*G01N 21/956* (2006.01)

(52) U.S. Cl.
CPC .......... *G01B 11/24* (2013.01); *G01N 21/95607* (2013.01); *G01B 2210/56* (2013.01); *G03F 7/70633* (2013.01)

USPC ............................ 356/399; 356/369; 356/401

(58) Field of Classification Search
None
See application file for complete search history.

(56) References Cited

U.S. PATENT DOCUMENTS

| 6,891,627 | B1 * | 5/2005 | Levy et al. ................... 356/625 |
| 7,042,569 | B2 | 5/2006 | Sezginer et al. |
| 7,236,244 | B1 | 6/2007 | Yang et al. |
| 7,277,172 | B2 | 10/2007 | Kandel et al. |
| 7,317,531 | B2 | 1/2008 | Mieher et al. |
| 2005/0157297 | A1 | 7/2005 | Abdulhalim et al. |
| 2006/0066855 | A1 | 3/2006 | Boef et al. |
| 2006/0274310 | A1 * | 12/2006 | Kandel et al. ................. 356/369 |
| 2008/0049233 | A1 | 2/2008 | De Groot |
| 2011/0310388 | A1 * | 12/2011 | Hill et al. ..................... 356/369 |

FOREIGN PATENT DOCUMENTS

| JP | 2006060214 | 3/2006 |
| JP | 2008542790 A | 11/2008 |
| WO | 2006133258 A2 | 12/2006 |
| WO | 2009100867 | 8/2009 |

* cited by examiner

Primary Examiner — Gordon J Stock, Jr.
(74) Attorney, Agent, or Firm — Suiter Swantz pc llo

(57) ABSTRACT

A method for determining an overlay offset may include, but is not limited to: obtaining a first anti-symmetric differential signal ($\Delta S_1$) associated with a first scatterometry cell; obtaining a second anti-symmetric differential signal ($\Delta S_2$) associated with a second scatterometry cell and computing an overlay offset from the first anti-symmetric differential ($\Delta S_1$) signal associated with the first scatterometry cell and the second anti-symmetric differential signal ($\Delta S_2$) associated with the second scatterometry cell.

17 Claims, 23 Drawing Sheets

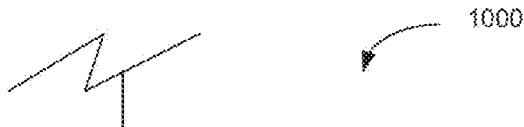

1020 obtaining a second anti-symmetric differential signal ($\Delta S_2$) associated with a second scatterometry cell

1230 obtaining scattering signals generated by a second scatterometry cell in response illumination by a first illumination beam and scattering signals generated by the second scatterometry cell in response to illumination by a second illumination beam

1350 illuminating the second scatterometry cell with an illumination beam having the first polarization

1360 imparting a second polarization to scattering signals generated by the second scatterometry cell in response to illumination by an illumination beam having the first polarization

1370 illuminating the second scatterometry cell with an illumination beam having the second polarization

1380 imparting the first polarization to scattering signals generated by the second scatterometry cell in response to illumination by an illumination beam having the second polarization

1240 computing a second differential signal ($\Delta S_2$) between: the scattering signals generated by the second scatterometry cell in response to illumination by the first illumination beam and the scattering signals generated by the second scatterometry cell in response to illumination by the second illumination beam

1030 computing an overlay offset from the first anti-symmetric differential ($\Delta S_1$) signal associated with the first scatterometry cell and the second anti-symmetric differential signal ($\Delta S_2$) associated with the second scatterometry cell

FIG. 13 (cont.)

ANGLE-RESOLVED ANTISYMMETRIC SCATTEROMETRY

RELATED APPLICATIONS

This application claims priority to Patent Cooperation Treaty Application No. PCT/US10/42738 filed on Jul. 21, 2010 which claims priority to U.S. Provisional Application Ser. No. 61/227,722 filed on Jul. 22, 2009, all of which are hereby incorporated by reference in their entirety.

BACKGROUND

Scatterometry is currently used in the semiconductor industry to measure thickness and optical properties of thin films as well as the critical dimension (CD) and profile shape of periodic structures on a semiconductor wafer. In principle, scatterometry has clear advantages over the current imaging technology of overlay metrology. Scatterometry may be capable of measuring device-size structures that cannot be resolved by imaging. Scatterometry may be also thought to be more robust to process variations and asymmetry in the profile of the measured structure.

Methods for measuring profile asymmetry include critical dimension scanning electron microscopy (CD-SEM) and scatterometry. The CD-SEM approach may be very slow and expensive. The current implementation of scatterometry CD metrology, which may be also suitable for monitoring properties of the profile (including profile asymmetry), relies on detailed modeling and may be therefore also rather slow. In addition, it may be very difficult to accurately model complicated profiles, such as two gratings (one on top of the other) separated by a layered possibly non-flat film.

SUMMARY

A method for determining an overlay offset may include, but is not limited to: obtaining a first anti-symmetric differential signal ($\Delta S_1$) associated with a first scatterometry cell; obtaining a second anti-symmetric differential signal ($\Delta S_2$) associated with a second scatterometry cell and computing an overlay offset from the first anti-symmetric differential ($\Delta S_1$) signal associated with the first scatterometry cell and the second anti-symmetric differential signal ($\Delta S_2$) associated with the second scatterometry cell.

It may be to be understood that both the foregoing general description and the following detailed description may be exemplary and explanatory only and may be not necessarily restrictive of the invention as claimed. The accompanying drawings, which may be incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which Figure Number:

1 shows a patterned scatterometry cell;
2A shows a scatterometry target including patterned scatterometry cells;
2B shows a scatterometry target including patterned scatterometry cells;
2C shows a scatterometry target including patterned scatterometry cells;
3 shows a scatterometry system;
4 shows a scatterometry system;
5A shows polarizer configurations;
5B shows polarizer configurations;
6A shows polarizer configurations;
6B shows polarizer configurations;
7A shows an illumination pupil;
7B shows a collection pupil;
8A shows an illumination pupil;
8B shows a collection pupil;
9A shows an illumination pupil;
9B shows a collection pupil;
10 shows a method for conducting scatterometry;
11 shows a method for conducting scatterometry;
12 shows a method for conducting scatterometry;
13 shows a method for conducting scatterometry;
14 shows a method for conducting scatterometry;
15 shows a method for conducting scatterometry;
16 shows a method for conducting scatterometry;
17 shows a method for conducting scatterometry;
18 shows a method for conducting scatterometry;
19A shows a scatterometry system; and
19B shows a scatterometry system.

DETAILED DESCRIPTION OF THE INVENTION

In the following detailed description of exemplary embodiments, reference may be made to the accompanying drawings, which form a part hereof. In the several figures, like referenced numerals identify like elements. The detailed description and the drawings illustrate exemplary embodiments. Other embodiments may be utilized, and other changes may be made, without departing from the spirit or scope of the subject matter presented here. The following detailed description may be therefore not to be taken in a limiting sense, and the scope of the claimed subject matter may be defined by the appended claims. It will be understood that the following description may be not intended to limit the invention to the described embodiments. To the contrary, it may be intended to cover alternatives, modifications and equivalents as may be included within the spirit and scope of the invention as defined by the appended claims.

Figure 1:
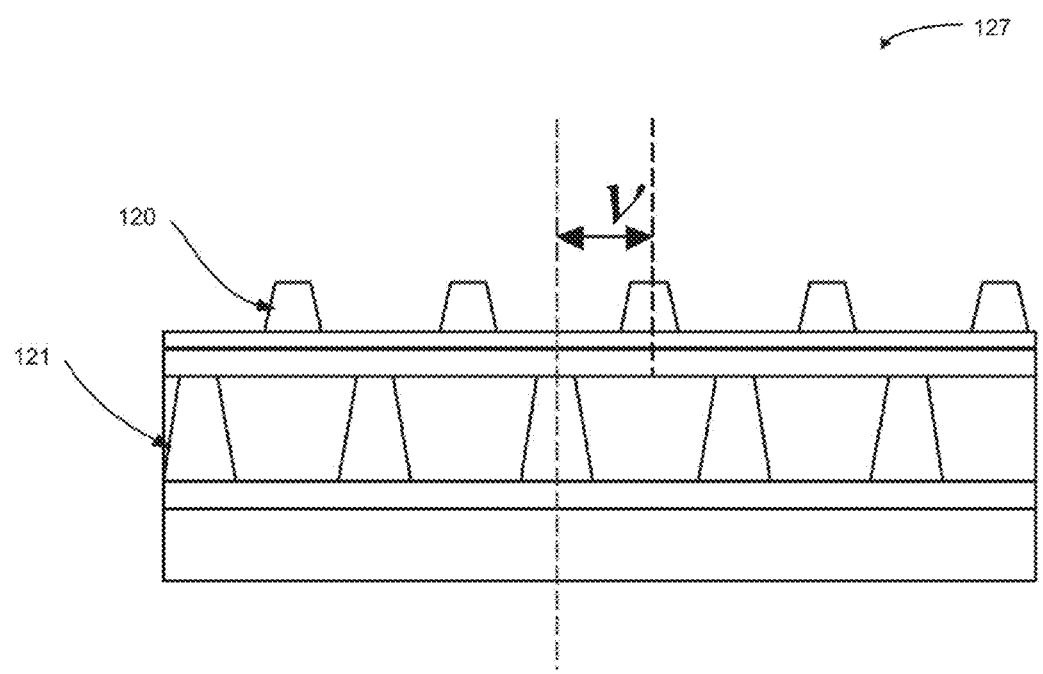

This invention is concerned with the measurement of differential-signal scatterometry overlay (SCOL). An overlay target may comprise one or more cells each having at least two patterns between which overlay is measured. Each cell may comprise two largely overlapping patterns, each of which may be in the same or different layers of the wafer. The geometric designs of the cells (pattern pitch, CD, etc.) may be identical, except for a programmed offset between the two patterns, which may vary from cell to cell. The two patterns may be referred to as the top and bottom patterns, and the overlay information refers to the shift between the top and bottom patterns. An exemplary overlay target is illustrated in FIG. 1. A top pattern 120 and a bottom pattern 121 may be shifted relative to each other by a total offset (v) including the programmed offset and any fabrication related overlay.

The total offset v of a cell may be the sum of two contributing factors: a programmed offset and an overlay offset (if present). The programmed offset may be designed into the cell. The overlay offset may be an unknown quantity to be determined which results from fabrication variations. Hence, in preparation for a scatterometry measurement according to an embodiment of the present invention, a target may be designed to comprise a plurality of cells, each of which has a programmed offset contributing to its total offset. Particular cells may have grating orientations orthogonal to one another (e.g. a first "horizontal" cell and a second "vertical" cell), for independent measurement of overlay in an x-direction and overlay in a Y-direction.

A scatterometry signal may be measured for each cell, and then differences between signals are calculated from which the value of the overlay may be extracted. The advantage of this method over other scatterometry methodologies is that the measurement of the overlay relies on symmetry characteristics between the measured signals themselves rather than a detailed comparison of the measured signals with simulated reference signals. As a result, no regression on or generation of a large library of simulated reference signals is required. However, such differential methodologies may require a large target consisting of several cells. As an example, a SCOL target may consist of 8 cells, 4 for X-overlay measurement and 4 for Y-overlay.

The architectures of this invention provide for multiple measurements on each cell in specific configurations that enable the extraction of one or more differential signals from each cell instead of a differential signal from a pair of cells. This may serve to reduce the number of cells required per target and hence the size of the target.

For example, two inspection signals may be employed to examine an overlay target. Inspection signal responses may be obtained for each inspection signal for each cell. It may be the case that a differential between a signal response associated with a first inspection signal and signal response associated with a second inspection signal may exhibit anti-symmetric properties as follows:

$$\Delta S(\text{offset}) = -\Delta S(-\text{offset})$$

Such differentials may vanish at offsets of zero and may be linear functions of offset for small values of the offset. The slope of such linear functions along with the overlay offset in a particular direction can be determined from measurements on two cells having different programmed offsets (i.e. two measured differential signals may be used to determine unknown slopes and overlays). As such, it may be desirable to provide systems and methods to generate signal responses exhibiting such anti-symmetric behavior to facilitate offset computation.

Figure 2A:
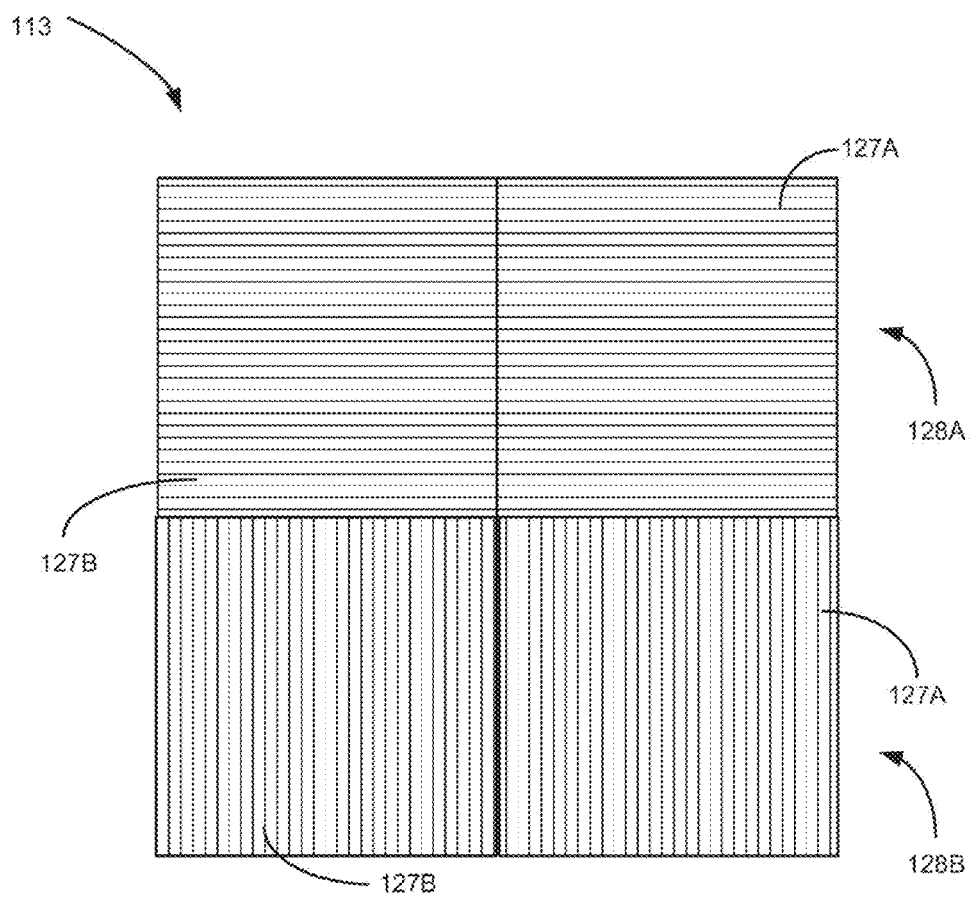

For example, as shown in FIG. 2A, an overlay target 113 may include multiple cells 127. The cells 127 may be arranged as cell pairs 128. The gratings of the cells 127 of cell pair 128A may be orthogonal to the gratings of the cells 127 of cell pair 128B to allow overlay measurement in both the x-direction and the y-direction. Each cell 127A may have a programmed offset $v_1$ between its top and bottom gratings and each cell 127B may have a programmed offset $v_2$, where $v_1 \ne v_2$. The combined use of an illumination beam having a first polarization and an illumination beam having a second polarization (as described below) to illuminate an overlay target 113 having such cell configurations may result in signal response differentials for each cell 127 which exhibit anti-symmetric behavior. Such anti-symmetric behavior may allow for zero-order scatterometry to be performed with only two cells 127 per direction as additional orthogonal information is provided by the sequential illumination of the overlay target 113 with the alternate polarization states.

Figure 2B:
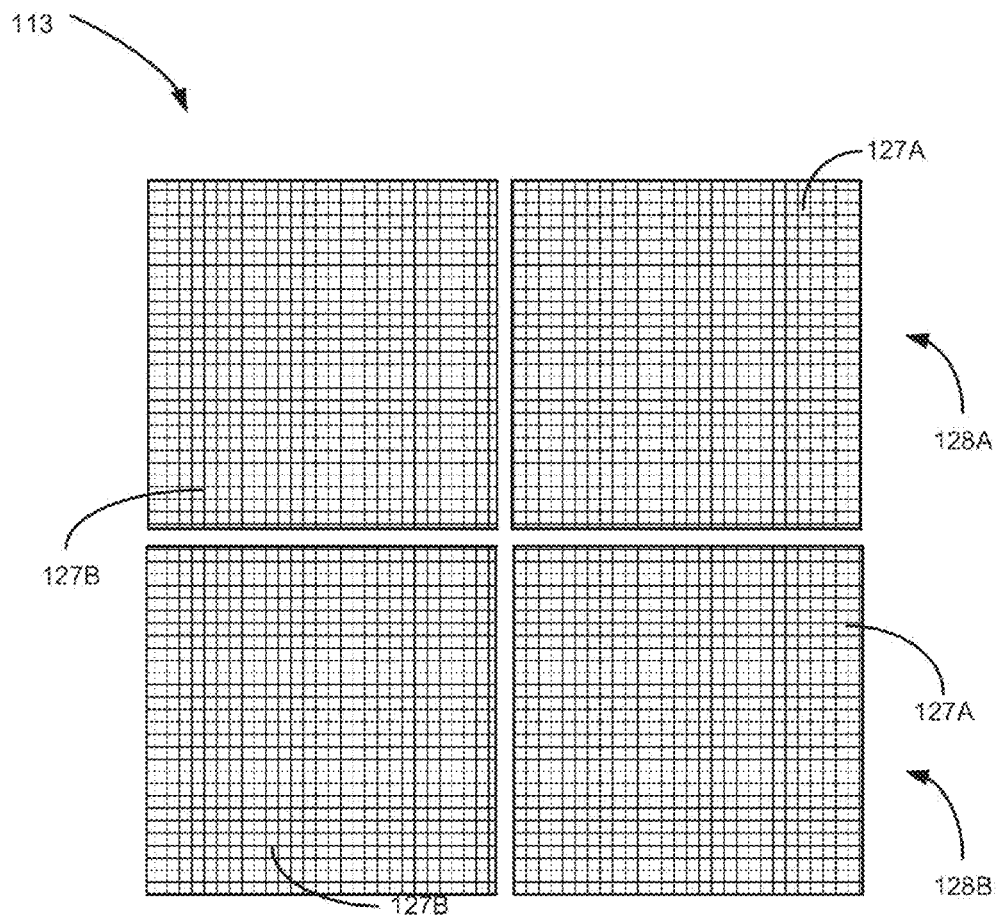

In a particular configuration shown in FIG. 2B, a first scatterometry cell 127A may include two-dimensional grating pattern having a first programmed offset (e.g. $v_1$) in a first direction (e.g. in the x-direction) and a second non-zero programmed offset (e.g. $v_2$) in a second direction orthogonal to the first direction (e.g. in a y-direction). Further, a second scatterometry cell 127B may include a two-dimensional grating pattern having a first programmed offset (e.g. $v_3$) in the first direction (e.g. in the x-direction) unequal to the first programmed offset of the first scatterometry cell (e.g. $v_1 \ne v_3$) and a second non-zero programmed offset (e.g. $v_4$) in the second direction (e.g. in the y-direction) equal to the second programmed offset of the first scatterometry cell (e.g. $v_2 = v_4$).

Figure 2C:
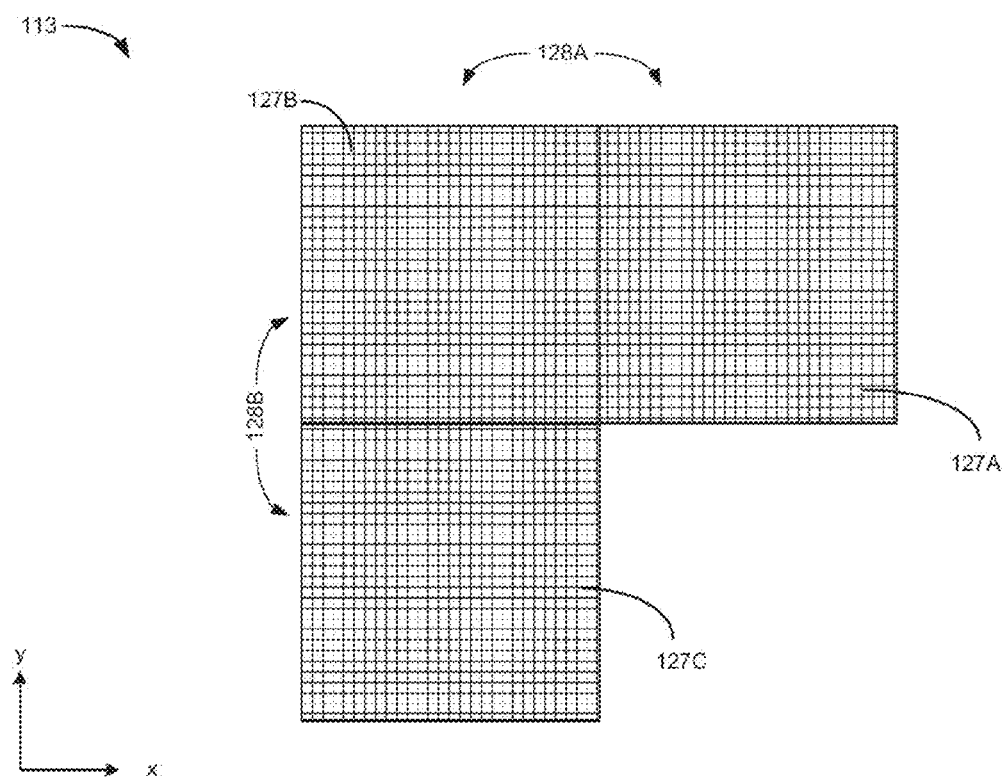

In an alternate configuration shown in FIG. 2C, an overlay target 113 may include a first cell 127A, a second cell 127B and a third cell 127C. Each cell 127 may include a two-dimensional grating. The three cells 127 may each have programmed offsets in both the x-direction and the y-direction. The programmed offsets may be configured such that the measurement of overlay offset in the x-direction utilizes cell 127A and cell 127B while the measurement of overlay offset in the y-direction utilizes cell 127B and cell 127C. The programmed offset of a cell i in the x-direction and the y-direction may be noted as $v_i^{(x)}$, and $v_i^{(y)}$, respectively. A particular example of the respective programmed offsets of a three-cell configuration may be as follows:

$$v_1^{(x)} = -v_2^{(x)} = -v_3^{(x)} f_0^{(x)}; v_1^{(y)} = v_2^{(y)} = -v_3^{(y)} = f_0^{(y)}$$

where $f_0^{(x)}$ and $f_0^{(y)}$ are the fundamental offsets in the x-direction and the y-direction, respectively. The fundamental offsets $f_0^{(x)}$ and $f_0^{(y)}$ may be significantly smaller than the pattern pitches for the gratings of the scatterometry cells 127. For example, the fundamental offsets $f_0^{(x)}$ and $f_0^{(y)}$ may be of the order of from 10 nm-15 nm.

Figure 3:
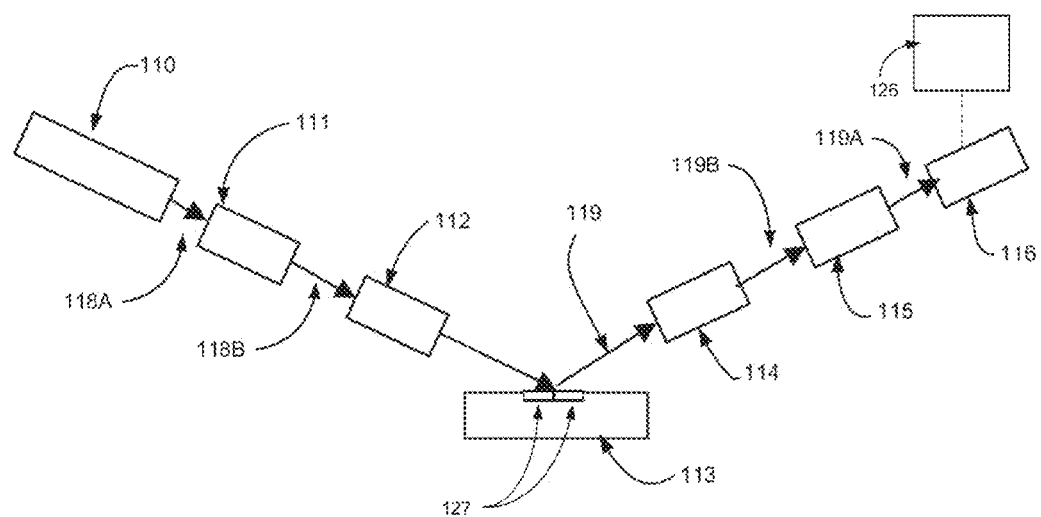

FIG. 3 shows a high-level block diagram illustrating a scatterometry system. The system may comprise a polarizer 111 on the illumination side and a polarizer 115 on the collection side. The polarizer 111 and the polarizer 115 may be configured to impart various polarizations on incident light. The incident light 118 emitted from a light source 110 may travel through the polarizer 111 and focusing optics 112, and may be scattered by a sample. The sample may be a semiconductor wafer comprising at least one overlay target 113. Interaction of the incident light 118 with one or more scatterometry cells 127 of an overlay target 113 may scatter incident light 118 thereby modifying the state of polarization of the incident light 118. The scattered light 119 may travel through collection optics 114 and a polarizer 115 where it may be detected by detector 116.

Figure 4:
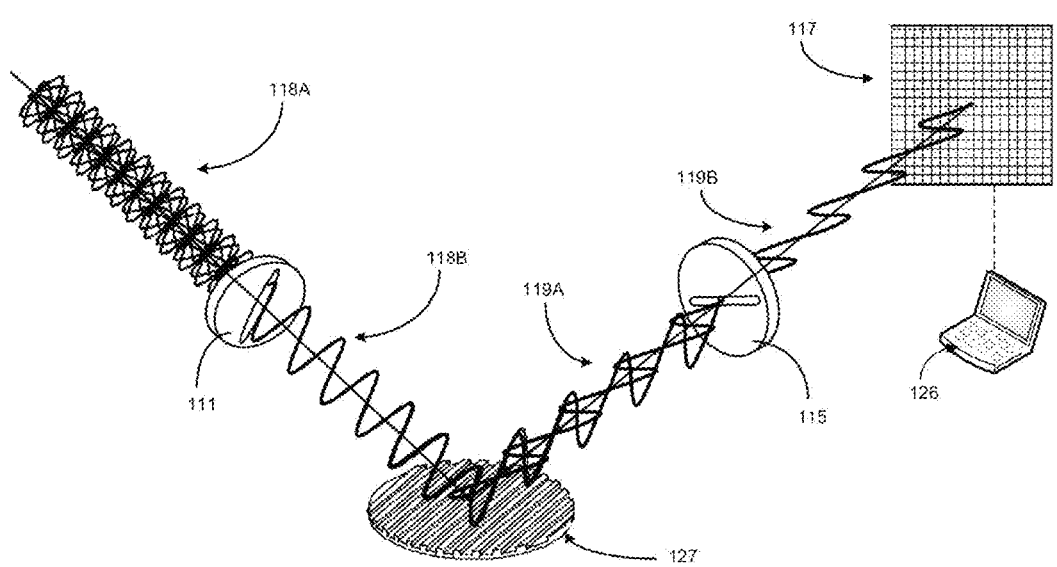

FIG. 4 shows another diagrammatic representation of a configuration of a scatterometry system showing the change in the state of light polarization before and after interaction with a scatterometry cell 127 of an overlay target 113, and showing a charge-coupled device (CCD) detector 116 for detecting the scattered light 119. For example, the polarizer 111 and may be configured to impart a first polarization to the incident light 118A resulting in polarized light 118B (e.g. vertically polarized light). The polarizer 115 may impart a second polarization to the scattered light 119A. Various polarization combinations for the polarizer 111 and the polarizer 115 may be employed. For example the polarizer 111 and the polarizer 115 may impart the following respective polarizations: horizontal/vertical, vertical/horizontal, azimuthal/radial, and/or radial azimuthal.

Figure 10:
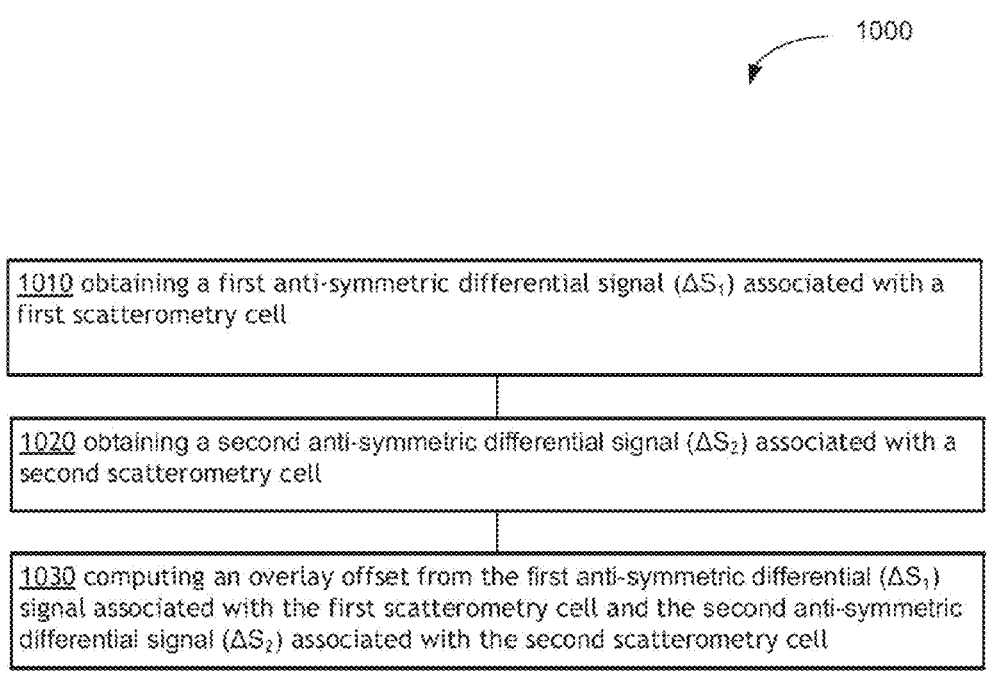
Figure 11:
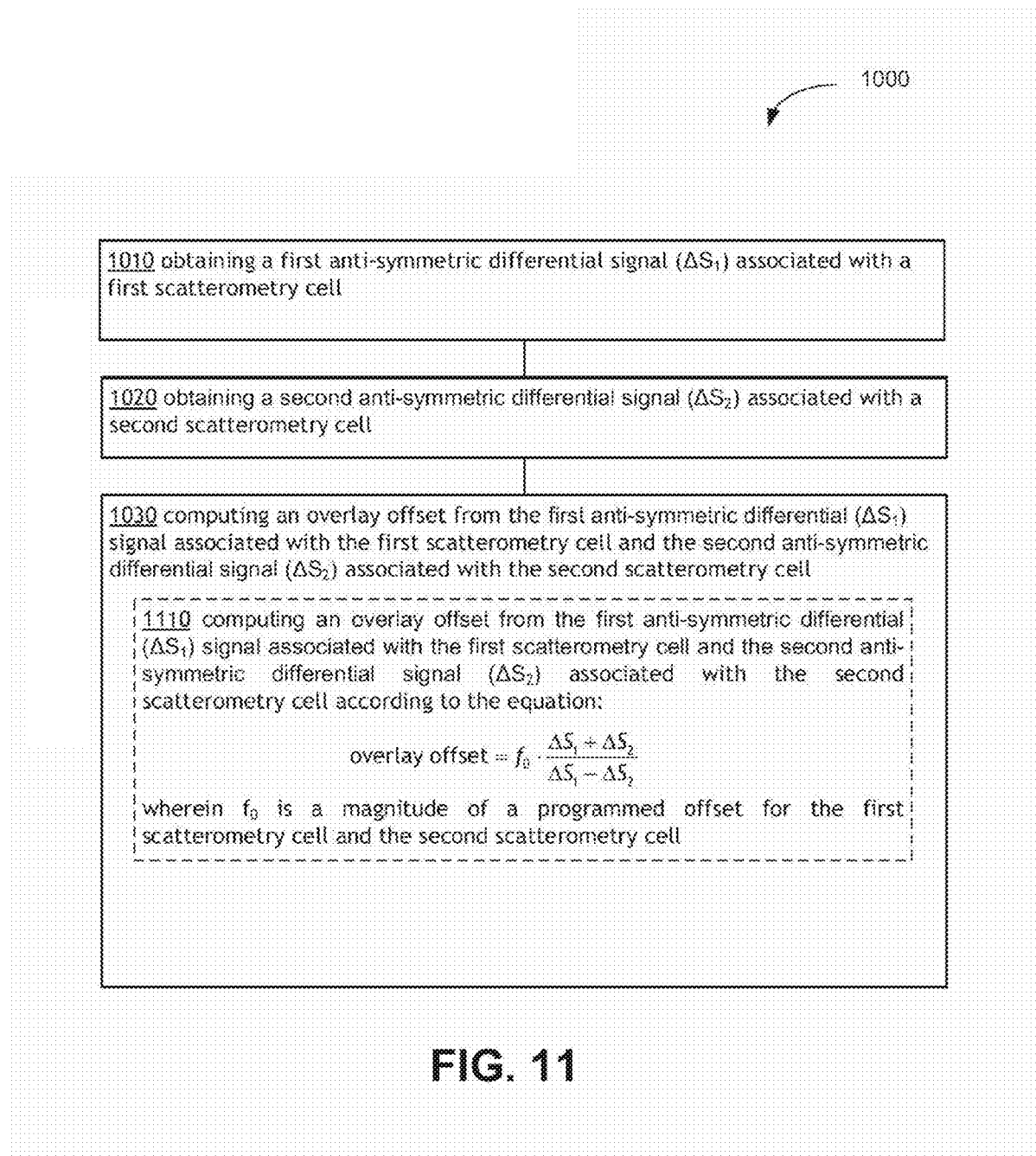

Anti-symmetric differential signals used to compute the target overlay offset may be obtained by conducting two measurements on a cell utilizing various optical configurations of an illumination path and a collection path of a scatterometry system as described below. Referring to FIG. 10, a method 1000 for estimating overlay offset of a sample using anti-symmetric differential signals is illustrated.

The operational flows, discussion and explanation may be provided with respect to the exemplary FIGS. 1-9B, and/or with respect to other examples and contexts. It should be understood that the operational flows may be executed in a number of other environments and contexts, and/or in modified versions of FIGS. 1-9B. In addition, although the various operational flows are presented in the sequence(s) illustrated, it should be understood that the various operations may be performed in orders and combinations other than those that are illustrated. For example, any operational step may be combined with any other operational step in any order.

Referring to FIG. 10, operation 1010 depicts obtaining a first anti-symmetric differential signal ($\Delta S_1$) associated with a first scatterometry cell. For example, as shown in FIGS. 1-4, a light source 110 may illuminate a first scatterometry cell 127A of a cell pair 128 with a first beam of incident light 118 (e.g. a beam having a first polarization) to generate scattered light 119. A CCD detector 116 may receive the scattered light 119 and convert that light into electrical signals to be processed by a computing device 126. Further, the light source 110 may illuminate the first scatterometry cell 127A of a cell pair 128 with a second beam of incident light 118 (e.g. a beam having a second polarization) to generate scattered light 119. A CCD detector 116 may receive the scattered light 119 and convert that light into electrical signals to be processed by a computing device 126. The computing device 126 may receive the electronic signal responses associated with each illumination of the scatterometry cell 127A and compute a differential between the signals.

Operation 1020 depicts obtaining a second anti-symmetric differential signal ($\Delta S_2$) associated with a second scatterometry cell. For example, as shown in FIGS. 1-4, a light source 110 may illuminate a second scatterometry cell 127B of a cell pair 128 with a first beam of incident light 118 (e.g. a beam having a first polarization) to generate scattered light 119. A CCD detector 116 may receive the scattered light 119 and convert that light into electrical signals to be processed by a computing device 126. Further, the light source 110 may illuminate the second scatterometry cell 127B of a cell pair 128 with a second beam of incident light 118 (e.g. a beam having a second polarization) to generate scattered light 119. A CCD detector 116 may receive the scattered light 119 and convert that light into electrical signals to be processed by a computing device 126. The computing device 126 may receive the electronic signal responses associated with each illumination of the scatterometry cell 127B and compute a differential between the signals.

Operation 1030 depicts computing an overlay offset from the first anti-symmetric differential ($\Delta S_1$) signal associated with the first scatterometry cell and the second anti-symmetric differential signal ($\Delta S_2$) associated with the second scatterometry cell. For example, as shown at Operation 1110, in the case of a first cell 127A and a second cell 127B of a cell pair 128A having programmed offsets $v_1 = f_0$ and $v_1 = -f_0$ in a given direction and differential signals $\Delta S_1$ (as determined in Operation 1010) and $\Delta S_2$ (as determined in Operation 1020) which are anti-symmetric, if both the overlay and the programmed offsets are small, it may be assumed that the differential signals are linear functions of the total offsets:

$$\Delta S_1 \propto f_0 + \text{overlay}; \Delta S_2 \propto -f_0 + \text{overlay}.$$

Therefore, the overlay offset of a cell pair 128 (e.g. along the x-direction) may be computed as:

$$\text{overlay offset} = f_0 \cdot \frac{\Delta S_1 + \Delta S_2}{\Delta S_1 - \Delta S_2}.$$

Figure 12:
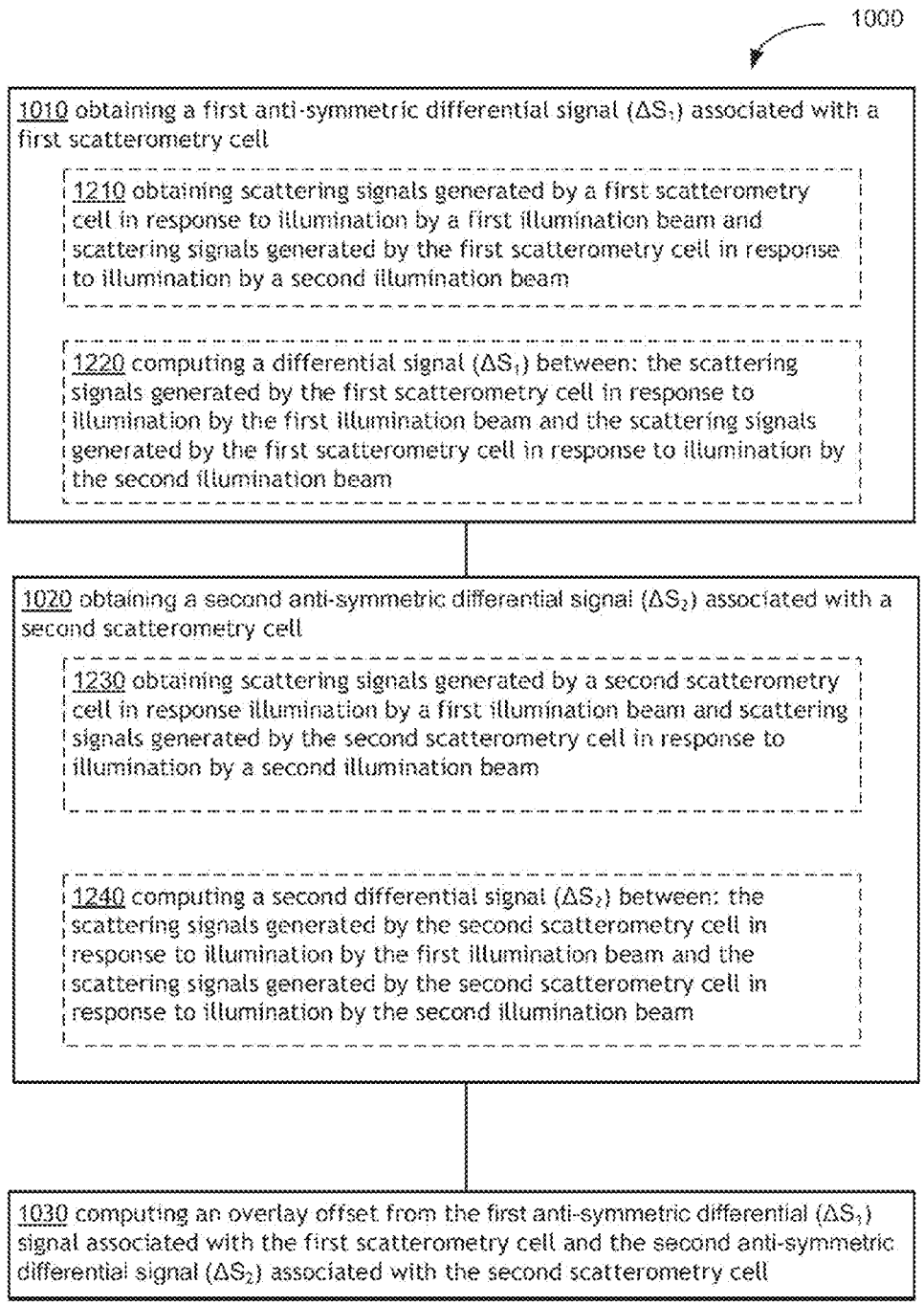

In one embodiment, obtaining a first anti-symmetric differential signal ($\Delta S_1$) associated with a first scatterometry cell of operation 1010 may include additional operations 1210 and 1220, and obtaining a second anti-symmetric differential signal ($\Delta S_2$) associated with a second scatterometry cell of operation 1020 may include additional operations 1230 and 1240 as shown in FIG. 12.

Operation 1210 depicts obtaining scattering signals generated by a first scatterometry cell in response to illumination by a first illumination beam and scattering signals generated by the first scatterometry cell in response to illumination by a second illumination beam. For example, as shown in FIGS. 1-4, a light source 110 may illuminate a first scatterometry cell 127A of a cell pair 128 with a first beam of incident light 118 (e.g. a beam having a first polarization) to generate scattered light 119. A CCD detector 116 may receive the scattered light 119 and convert that light into electrical signals to be processed by a computing device 126. Further, the light source 110 may illuminate the first scatterometry cell 127A of a cell pair 128 with a second beam of incident light 118 (e.g. a beam having a second polarization) to generate scattered light 119. A CCD detector 116 may receive the scattered light 119 and convert that light into electrical signals to be processed by a computing device 126.

Operation 1220 depicts computing a differential signal ($\Delta S_1$) between: the scattering signals generated by the first scatterometry cell in response to illumination by the first illumination beam and the scattering signals generated by the first scatterometry cell in response to illumination by the second illumination beam. For example, the computing device 126 may receive first electronic signals from the detector 116 generated in response to scattering of a first illumination beam (e.g. a beam having a first polarization) by a first cell 127A of a cell pair 128. The computing device 126 may further receive second electronic signals from the detector 116 generated in response to scattering of a second illumination beam (e.g. a beam having a second polarization) by the first cell 127A of a cell pair 128. The computing device 126 may carry out one or more optimization computations on the first and second electronic signals (e.g. normalization, subtraction of dark signals, etc.) to remove background effects, noise, and the like. Following such computations, the computing device 126 may then compute a differential between the first electronic signals and the second electronic signals.

Operation 1230 depicts obtaining scattering signals generated by a second scatterometry cell in response illumination by a first illumination beam and scattering signals generated by the second scatterometry cell in response to illumination by a second illumination beam. For example, as shown in FIGS. 1-4, a light source 110 may illuminate a second scatterometry cell 127B of a cell pair 128 with a first beam of incident light 118 (e.g. a beam having a first polarization) to generate scattered light 119. A CCD detector 116 may receive the scattered light 119 and convert that light into electrical signals to be processed by a computing device 126. Further, the light source 110 may illuminate the second scatterometry cell 127B of a cell pair 128 with a second beam of incident light 118 (e.g. a beam having a second polarization) to generate scattered light 119. A CCD detector 116 may receive the scattered light 119 and convert that light into electrical signals to be processed by a computing device 126.

Operation 1240 depicts computing a second differential signal ($\Delta S_2$) between: the scattering signals generated by the second scatterometry cell in response to illumination by the first illumination beam and the scattering signals generated by the second scatterometry cell in response to illumination by the second illumination beam. For example, the computing device 126 may receive first electronic signals from the detector 116 generated in response to scattering of a first illumination beam (e.g. a beam having a first polarization) by a second cell 127B of a cell pair 128. The computing device 126 may further receive second electronic signals from the detector 116 generated in response to scattering of a second illumination beam (e.g. a beam having a second polarization) by the second cell 127B of a cell pair 128. The computing device 126 may then compute a differential between the first electronic signals and the second electronic signals.

Figure 13:
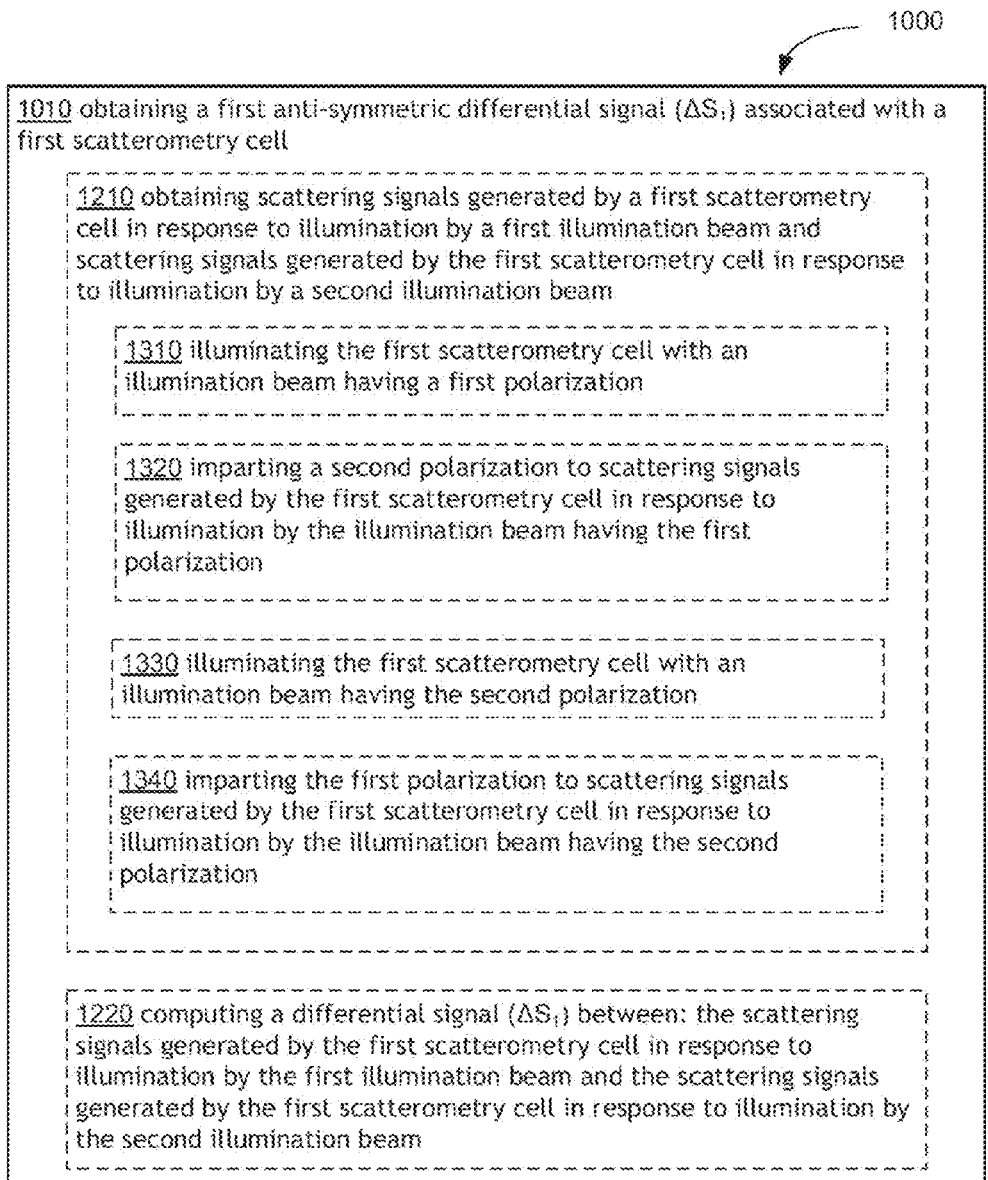

In an embodiment, obtaining scattering signals generated by a first scatterometry cell in response to illumination by a first illumination beam and scattering signals generated by the first scatterometry cell in response to illumination by a second illumination beam of operation 1210 may include additional operations 1310-1340, and obtaining scattering signals generated by a second scatterometry cell in response illumination by a first illumination beam and scattering signals generated by the second scatterometry cell in response to illumination by a second illumination beam of operation 1230 may include additional operations 1350-1380 as shown in FIG. 13.

Operation 1310 depicts illuminating the first scatterometry cell with an illumination beam having a first polarization. For example, as shown in FIGS. 2-6B, the polarizer 111 may be configured to impart a first polarization to the incident light 118A resulting in polarized light 118B having the first polarization. The rotational angle of the polarizer 111 may be adjusted to specify the particular polarization configuration. The polarized light 118B may be directed towards a first cell 127A of a cell pair 128 (e.g. cell pair 128A) of an overlay target 113 by focusing optics 112 so as to illuminate the first cell 127A. The polarized light 118B may be scattered by the first cell 127A resulting in scattered light 119A.

Operation 1320 depicts imparting a second polarization to scattering signals generated by the first scatterometry cell in response to illumination by the illumination beam having the first polarization. For example, as shown in FIGS. 2-6B, the polarizer 115 may be configured to impart a second polarization to the scattered light 119A resulting in polarized scattered light 119B having the second polarization. The rotational angle of the polarizer 111 may be adjusted to specify the particular polarization configuration.

Operation 1330 depicts illuminating the first scatterometry cell with an illumination beam having the second polarization. For example, as shown in FIGS. 2-6B, the polarizer 111 may be configured to impart the second polarization previously imparted to the scattered light 119A by the polarizer 115 (e.g. as in Operation 1015) to the incident light 118A resulting in polarized light 118B having the second polarization. The rotational angle of the polarizer 111 may be adjusted to specify the particular polarization configuration. The polarized light 118B having the second polarization may be directed towards the first cell 127A of the overlay target 113 by focusing optics 112 so as to illuminate the first cell 127A. The polarized light 118B may be scattered by the first cell 127A resulting in scattered light 119A.

Operation 1340 depicts imparting the first polarization to scattering signals generated by the first scatterometry cell in response to illumination by an illumination beam having the second polarization. For example, as shown in FIGS. 2-6B, the polarizer 115 may be configured to impart the first polarization previously applied to the incident light 118A by the polarizer 111 (e.g. as in Operation 1010) to the scattered light 119A resulting in polarized scattered light 119B having the first polarization. The rotational angle of the polarizer 115 may be adjusted to specify the particular polarization configuration.

Figure 5A:
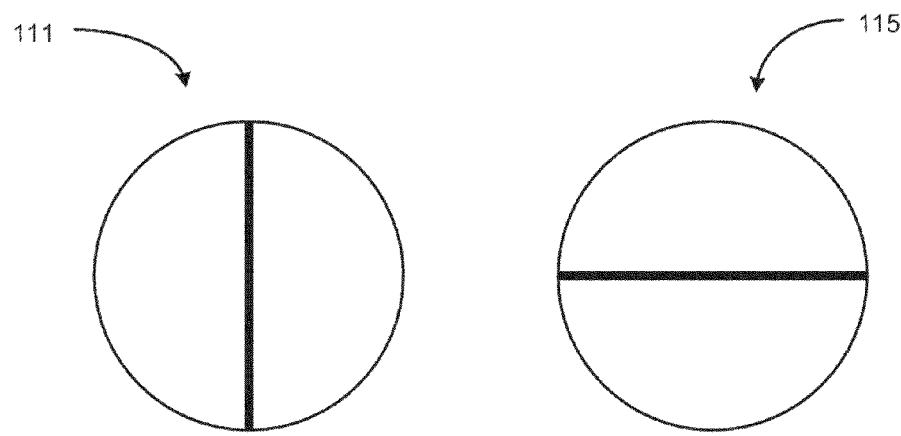
Figure 5B:
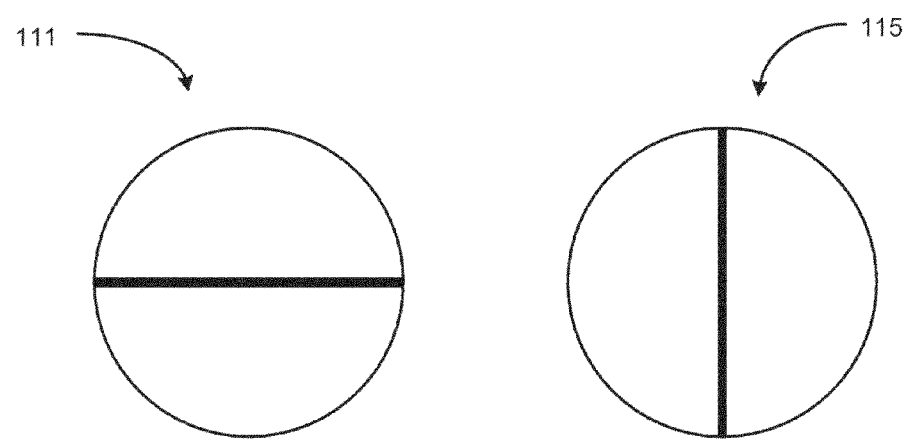

Referring to FIG. 5A, in a first scatterometry measurement associated with a first scatterometry cell (as previously described with respect to operations 1310-1320), the polarizer 111 may be configured to impart a first linear polarization (e.g. vertical polarization) to the incident light 118A and the polarizer 115 may be configured to impart a second linear polarization orthogonal to the first linear polarization (e.g. horizontal polarization) to the scattered light 119A. Referring to FIG. 5B, in a second scatterometry measurement associated with the first scatterometry cell (as previously described with respect to operations 1330-1340), the polarizer 111 may be configured to impart the second linear polarization (e.g. horizontal polarization) to the incident light 118A and the polarizer 115 may be configured to impart the first linear polarization orthogonal to the second polarization (e.g. vertical polarization) to the scattered light 119A.

Figure 6A:
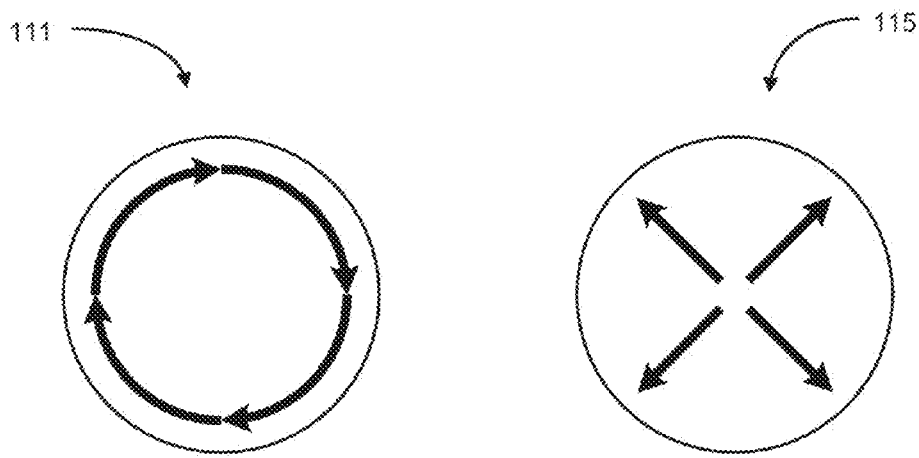
Figure 6B:
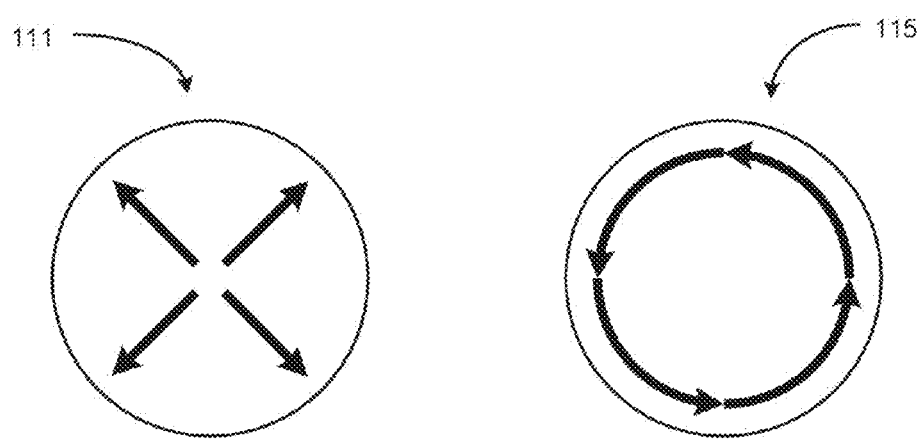

Alternately, referring to FIG. 6A, in a first scatterometry measurement associated with a first scatterometry cell (as previously described with respect to operations 1310-1320), the polarizer 111 may be configured to impart annular polarization to the incident light 118A and the polarizer 115 may be configured to impart a radial polarization to the scattered light 119A. Referring to FIG. 6B, in a second scatterometry measurement associated with the first scatterometry cell (as previously described with respect to operations 1330-1340), the polarizer 111 may be configured to impart the radial polarization to the incident light 118A and the polarizer 115 may be configured to impart the annular polarization to the scattered light 119A.

Operation 1350 depicts illuminating the second scatterometry cell with an illumination beam having the first polarization. For example, as shown in FIGS. 2-6B, polarizer 111 may be configured to impart a first polarization to the incident light 118A resulting in polarized light 118B having the first polarization. The rotational angle of the polarizer 111 may be adjusted to specify the particular polarization configuration. The polarized light 118B may be directed towards a second cell 127B of a cell pair 128 (e.g. cell pair 128A) of an overlay target 113 by focusing optics 112 so as to illuminate the second cell 127B. The polarized light 118B may be scattered by the second cell 127B resulting in scattered light 119A.

Operation 1360 depicts imparting the first polarization to scattering signals generated by the second scatterometry cell in response to illumination by an illumination beam having the second polarization. For example, as shown in FIGS. 2-6B, polarizer 115 may be configured to impart a second polarization to the scattered light 119A resulting in polarized scattered light 119B having the second polarization. The rotational angle of the polarizer 111 may be adjusted to specify the particular polarization configuration.

Operation 1370 depicts illuminating the second scatterometry cell with an illumination beam having the second polarization. For example, as shown in FIGS. 2-6B, the polarizer 111 may be configured to impart the second polarization previously imparted to the scattered light 119A by the polarizer 115 (e.g. as in Operation 1035) to the incident light 118A resulting in polarized light 118B having the second polarization. The rotational angle of the polarizer 111 may be adjusted to specify the particular polarization configuration. The polarized light 118B having the second polarization may be directed towards the second cell 127B of the overlay target 113 by focusing optics 112 so as to illuminate the second cell 127. The polarized light 118B may be scattered by the second cell 127B resulting in scattered light 119A.

Operation 1370 depicts imparting the first polarization to scattering signals generated by the second scatterometry cell in response to illumination by an illumination beam having the second polarization. For example, as shown in FIGS. 2-6B, polarizer 115 may be configured to impart the first polarization previously applied to the incident light 118A by the polarizer 111 (e.g. as in Operation 1030) to the scattered light 119A resulting in polarized scattered light 119B having the first polarization. The rotational angle of the polarizer 115 may be adjusted to specify the particular polarization configuration.

Referring to FIG. 5A, in a first scatterometry measurement associated with a second scatterometry cell (as previously described with respect to operations 1350-1360), the polarizer 111 may be configured to impart a first linear polarization (e.g. vertical polarization) to the incident light 118A and the polarizer 115 may be configured to impart a second linear polarization orthogonal to the first linear polarization (e.g. horizontal polarization) to the scattered light 119A. Referring to FIG. 5B, in a second scatterometry measurement associated with the second scatterometry cell (as previously described with respect to operations 1370-1380), the polarizer 111 may be configured to impart the second linear polarization (e.g. horizontal polarization) to the incident light 118A and the polarizer 115 may be configured to impart the first linear polarization orthogonal to the second polarization (e.g. vertical polarization) to the scattered light 119A.

Alternately, referring to FIG. 6A, in a first scatterometry measurement associated with a first scatterometry cell (as previously described with respect to operations 1350-1360), the polarizer 111 may be configured to impart annular polarization to the incident light 118A and the polarizer 115 may be configured to impart a radial polarization to the scattered light 119A. Referring to FIG. 6B, in a second scatterometry measurement associated with the first scatterometry cell (as previously described with respect to operations 1370-1380), the polarizer 111 may be configured to impart the radial polarization to the incident light 118A and the polarizer 115 may be configured to impart the annular polarization to the scattered light 119A.

Figure 14:
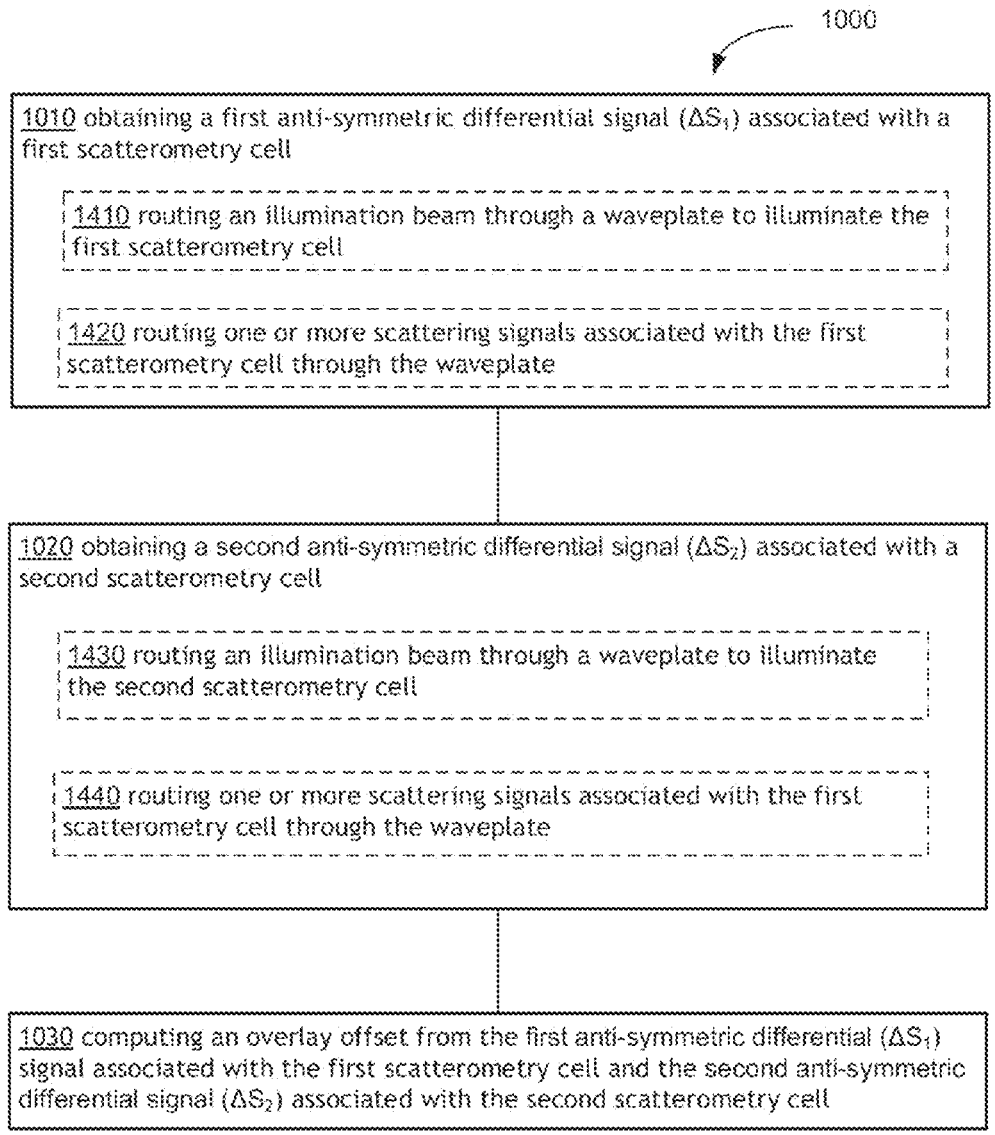

In an embodiment, obtaining scattering signals generated by a first scatterometry cell in response to illumination by a first illumination beam and scattering signals generated by the first scatterometry cell in response to illumination by a second illumination beam of operation 1210 may include additional operations 1410-1420, and obtaining scattering signals generated by a second scatterometry cell in response illumination by a first illumination beam and scattering signals generated by the second scatterometry cell in response to illumination by a second illumination beam of operation 1230 may include additional operations 1430-1440 as shown in FIG. 14.

In one embodiment, obtaining a first anti-symmetric differential signal ($\Delta S_1$) associated with a first scatterometry cell of operation 1010 may include additional operations 1410 and 1420, and obtaining a second anti-symmetric differential signal ($\Delta S_2$) associated with a second scatterometry cell of operation 1020 may include additional operations 1430 and 1440 as shown in FIG. 12.

Figure 19A:
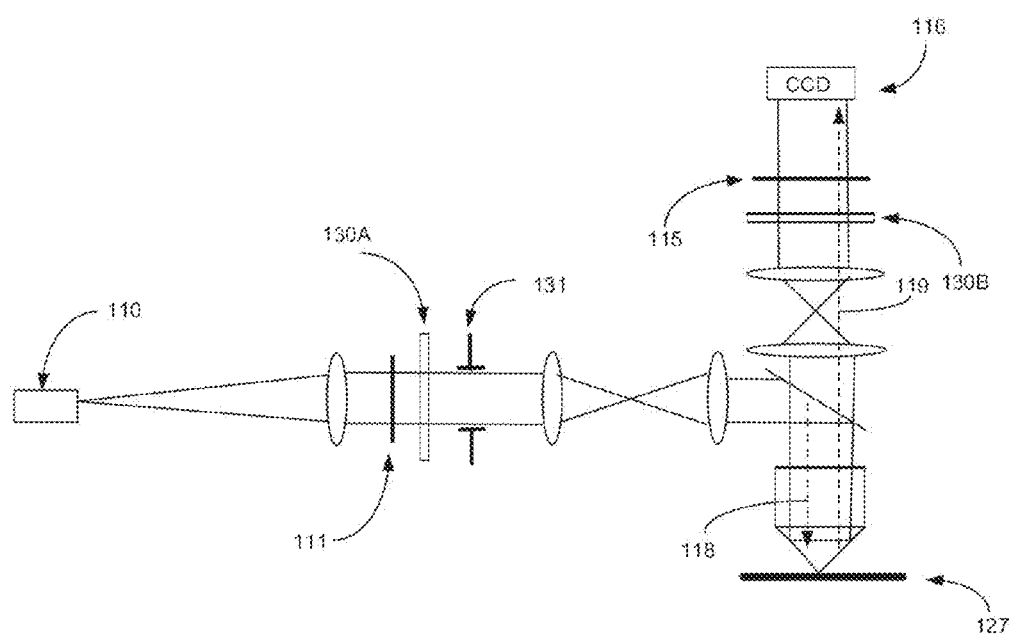

Operations 1410 and 1430 depict routing an illumination beam having at least one of the first polarization and the second polarization through at least one waveplate. Operation 1420 depicts routing one or more scattering signals through the at least one waveplate. For example, as shown in FIG. 19A, anti-symmetric differential signals may be obtained with an optical configuration that includes a polarizer 111 in the illumination path, a waveplate 130A (e.g. a quarter waveplate) in the illumination path, a waveplate 130B (e.g. a quarter waveplate) in the collection path and a polarizer 115 in the collection path. The polarizers and waveplates may be configured such that differential signals measured with proper angles of the polarizers and waveplates obey the anti-symmetry condition. For example, the angle of the polarizer 111 in the illumination path may be 0 degrees in a first measurement of a cell and 90 degrees in the second measurement of a cell. The angle of the polarizer 115 in the collection path may be 90 degrees in the first measurement of the cell and 0 degrees in the second measurement of the cell. The angle of the waveplate 130A in the illumination path may be 45 degrees for both measurements of the cell. The angle of the waveplate 130B in the collection path may be −135 degrees for both measurements of the cell. An advantage of such a measurement scheme is that it allows flexibility in the polarization and phase content of the signal for optimal sensitivity to overlay. In addition, such an optical configuration can be tuned to have optimal overlay sensitivity for relatively small angles of incidence. In this case, illumination pupil 122 apodization by an apodizing aperture 131 may be used to reduce spot size without loss of sensitivity to overlay.

Figure 19B:
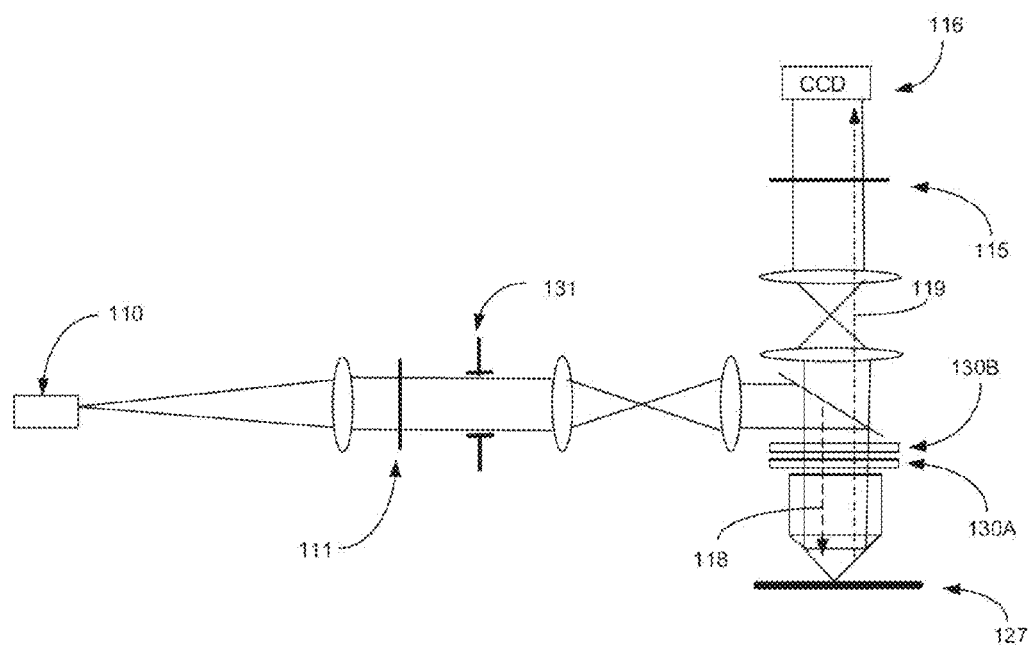

In an alternate configuration shown in FIG. 19B, the anti-symmetric differential signals may be obtained with an optical configuration that includes a polarizer 111 in the illumination path, a polarizer 115 in the collection path and at least two waveplates 130 (e.g. a half waveplate 130A a quarter waveplate 130B) in a location common to the illumination path and the collection path, so that both waveplates 130 are passed through twice (e.g. once by the incident light 118 before illuminating the wafer and a second time by the scattered light 119 following scattering of the incident light 118 by a scatterometry cell 127). For example, for a first measurement of a cell the polarizer 111 may be at 0 degrees, the half waveplate 130A at 205 degrees, the quarter waveplate 130B at 5 degrees and the polarizer 115 at 90 degrees. For a second measurement of the cell, the polarizer 111 may be at 90 degrees, the half waveplate 130A at 300 degrees, the quarter waveplate 130B at 15 degrees and the polarizer 115 at 0 degrees.

Figure 15:
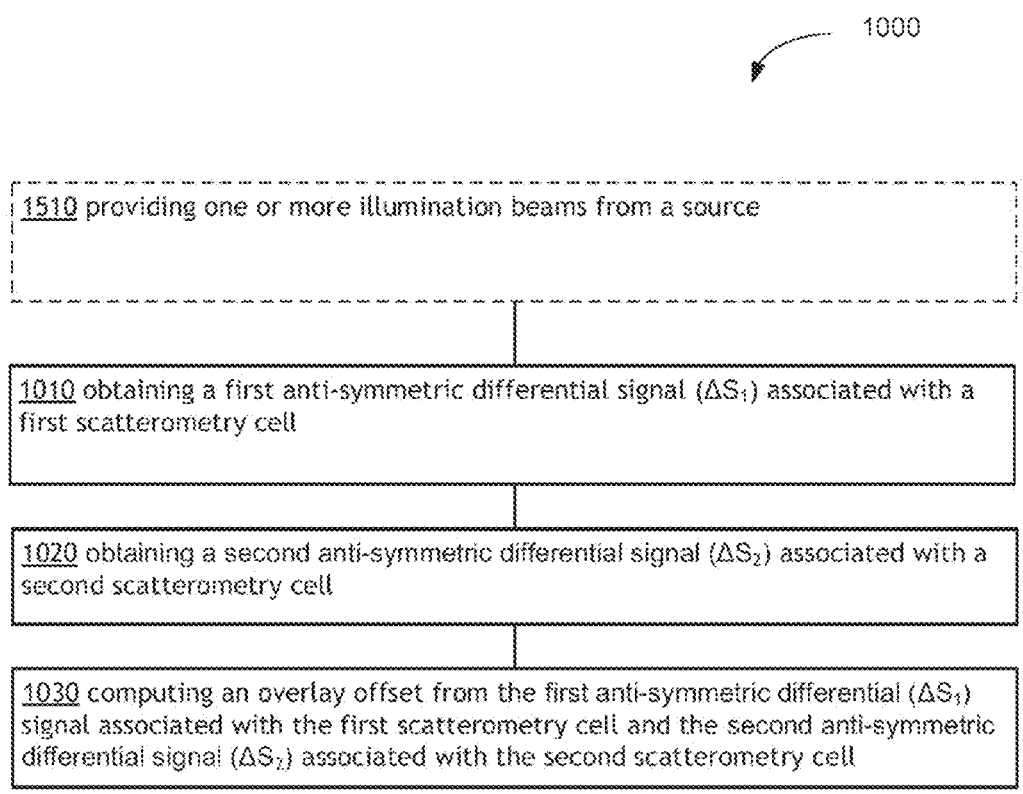

In an alternate embodiment, method 1000 may include an additional operation 1510 as shown in FIG. 15.

Figure 7A:
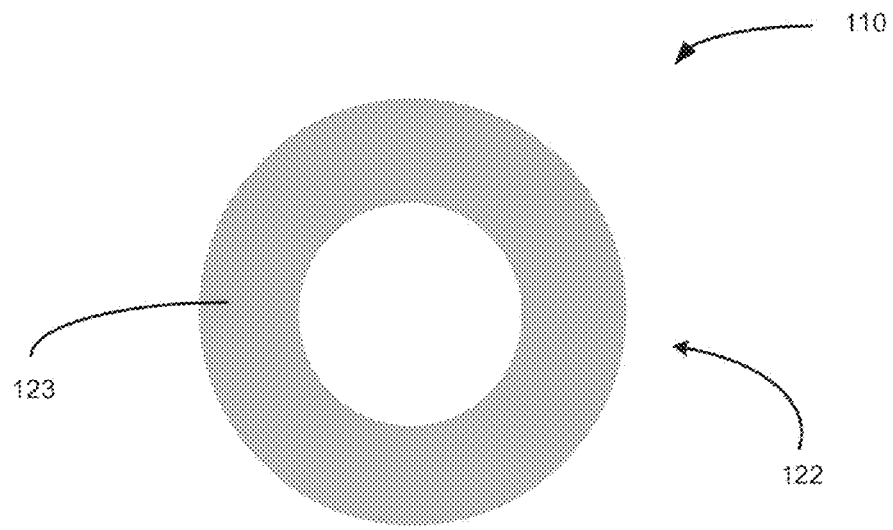
Figure 8A:
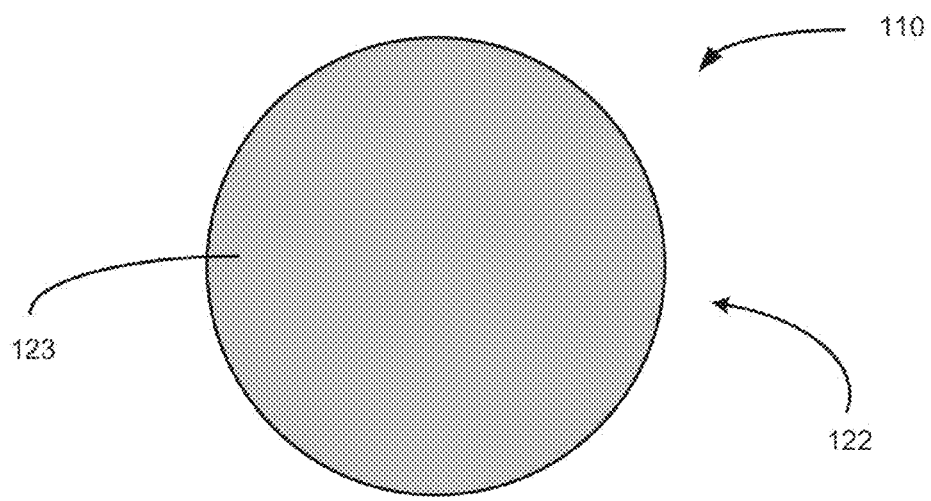
Figure 9A:
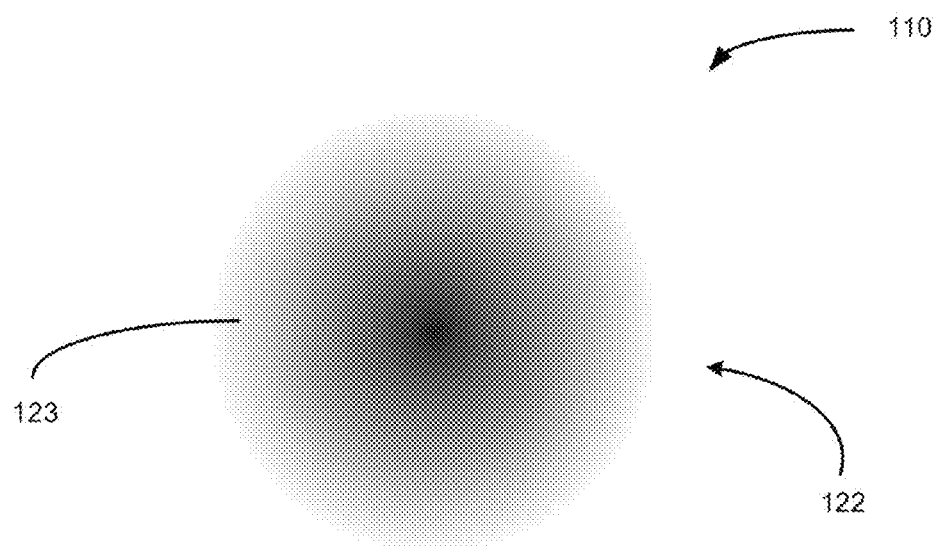

Operation 1510 depicts providing one or more illumination beams from a source. For example, the light source 110 may emit an incident light 118. As shown in FIG. 7A, the light source 110 may include an illumination pupil 122 having an annular portion 123. Use of an illumination pupil 122 including the annular portion 123 may allow for scattered signals to be measured at multiple positions in the pupil via specular reflection (i.e. zero-order diffraction). Alternately, as shown in FIG. 8A, a full illumination pupil 122 may be employed. Alternately, as shown in FIG. 9A, an apodized illumination pupil 122 may be employed. Further, incident light 118 may be a monochromatic illumination beam or an illumination beam including a sequence of multiple wavelengths.

Figure 16:
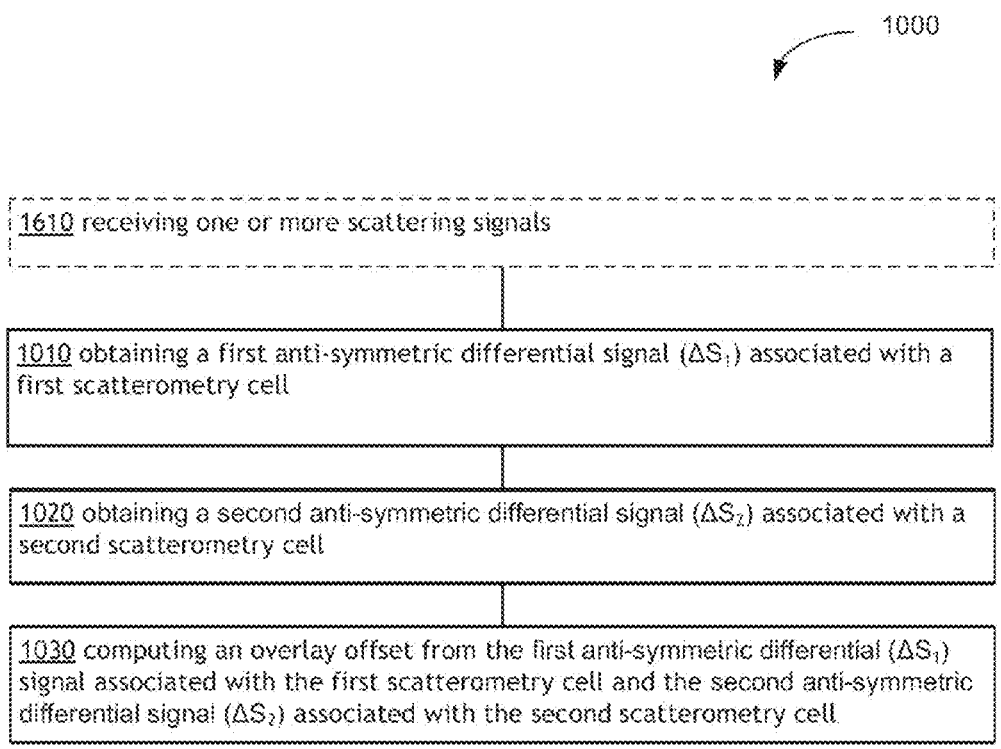

In an alternate embodiment, method 1000 may include an additional operation 1610 as shown in FIG. 16.

Figure 7B:
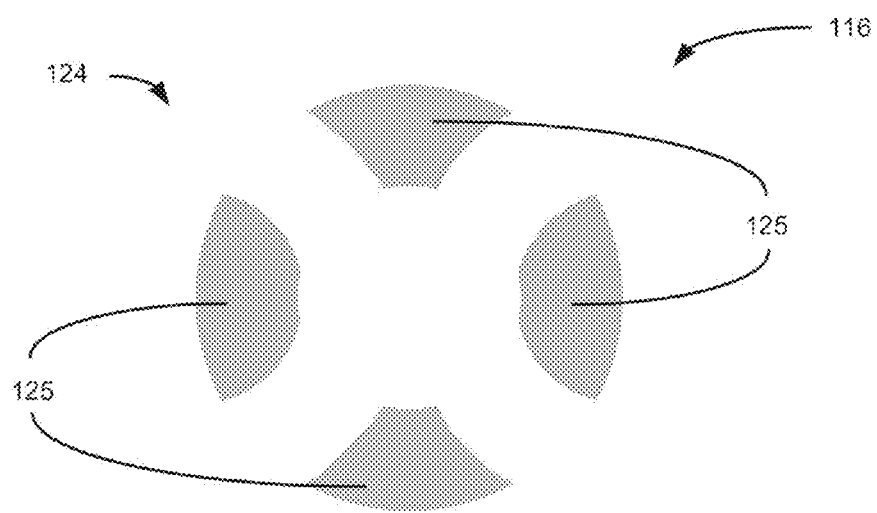
Figure 8B:
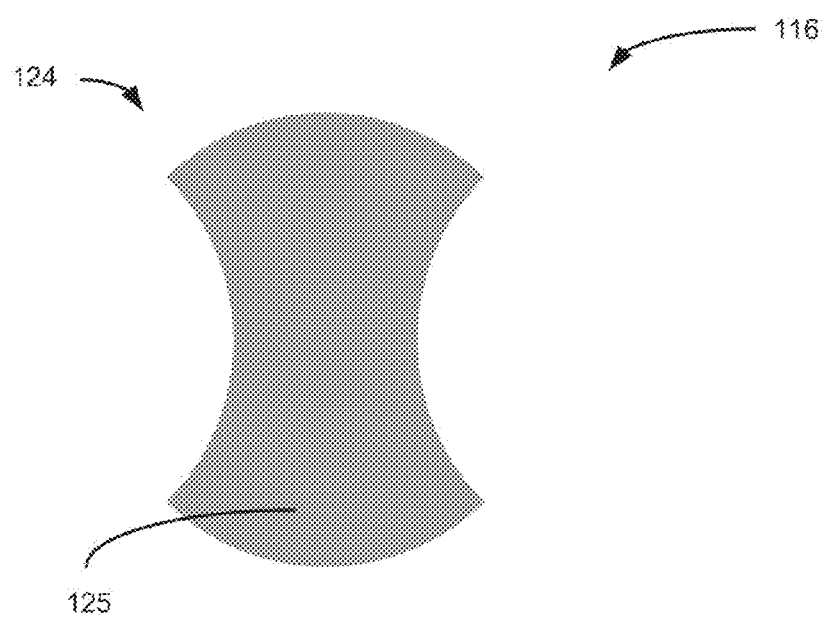
Figure 9B:
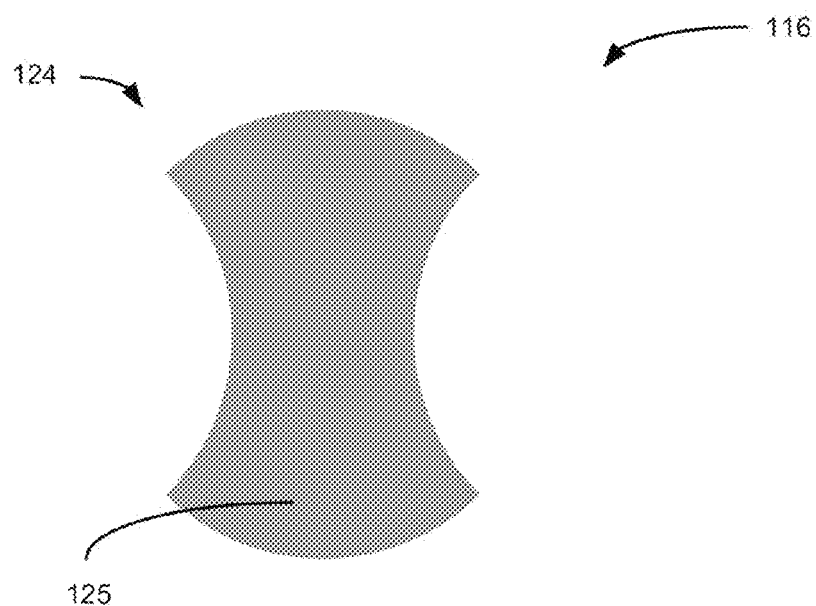

Operation 1610 depicts receiving one or more scattering signals. For example, as shown in FIGS. 3-4 and 7B, 8B and 9B, the CCD detector 116 may receive the scattered light 119B and convert that light into electrical signals to be processed by a computing device 126. As shown in FIG. 7B, the detector 116 may include a collection pupil 124 having apertures 125. A detector 116 including collection pupil 124 of FIG. 7B may be employed in combination with a light source 110 including the illumination pupil 122 of FIG. 7A. Alternately, as shown in FIG. 8B, the detector 116 may include a collection pupil 124 having light receiving pixels 125. A detector 116 including collection pupil 124 of FIG. 8B may be employed in combination with a light source 110 including the illumination pupil 122 of FIG. 8A. Alternately, as shown in FIG. 9B, the detector 116 may include a collection pupil 124 having light receiving pixels 125. A detector 116 including the collection pupil 124 of FIG. 9B may be employed in combination with a light source 110 including the illumination pupil 122 of FIG. 9A. A computing device 126 may receive electronic signals generated by the CCD detector 116 indicative of the light scattering characteristics of one or more scatterometry cells 127 of the overlay target 113. The computing device may compute one or more metrology characteristics of a sample (e.g. overlay offset, critical distance and the like) from the electronic signals.

Figure 17:
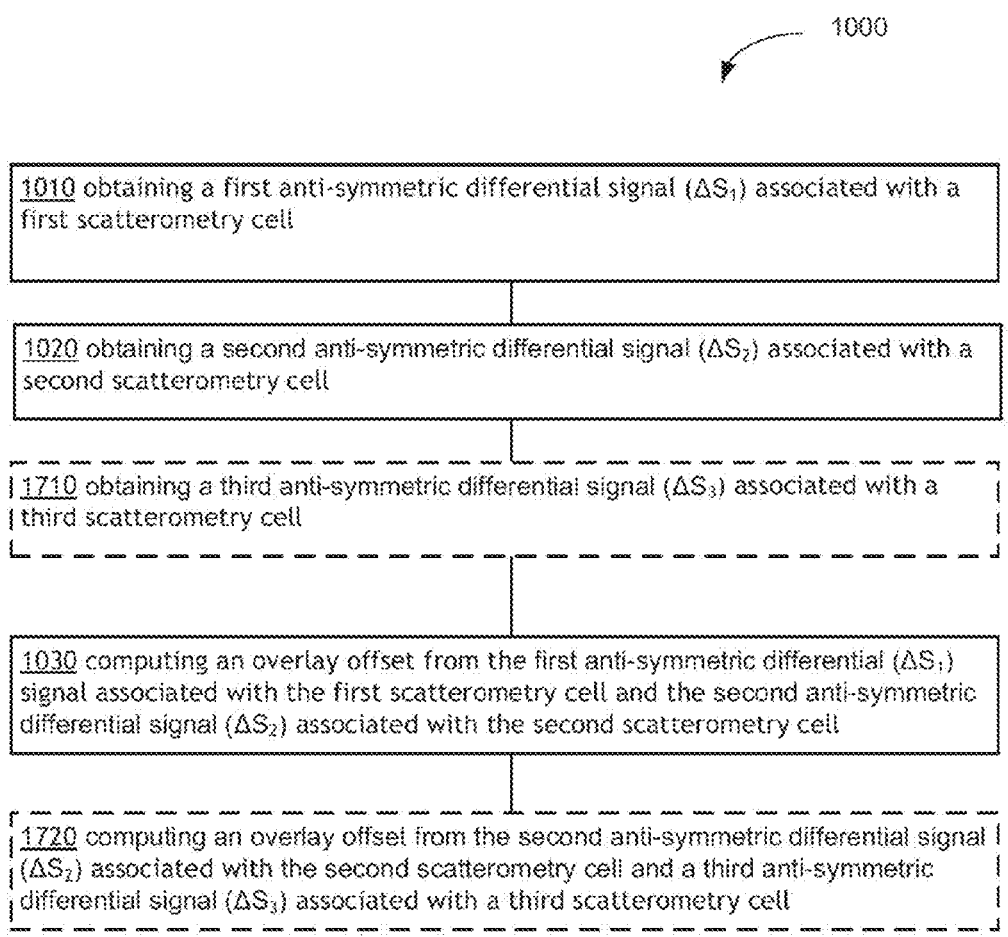
Figure 18:
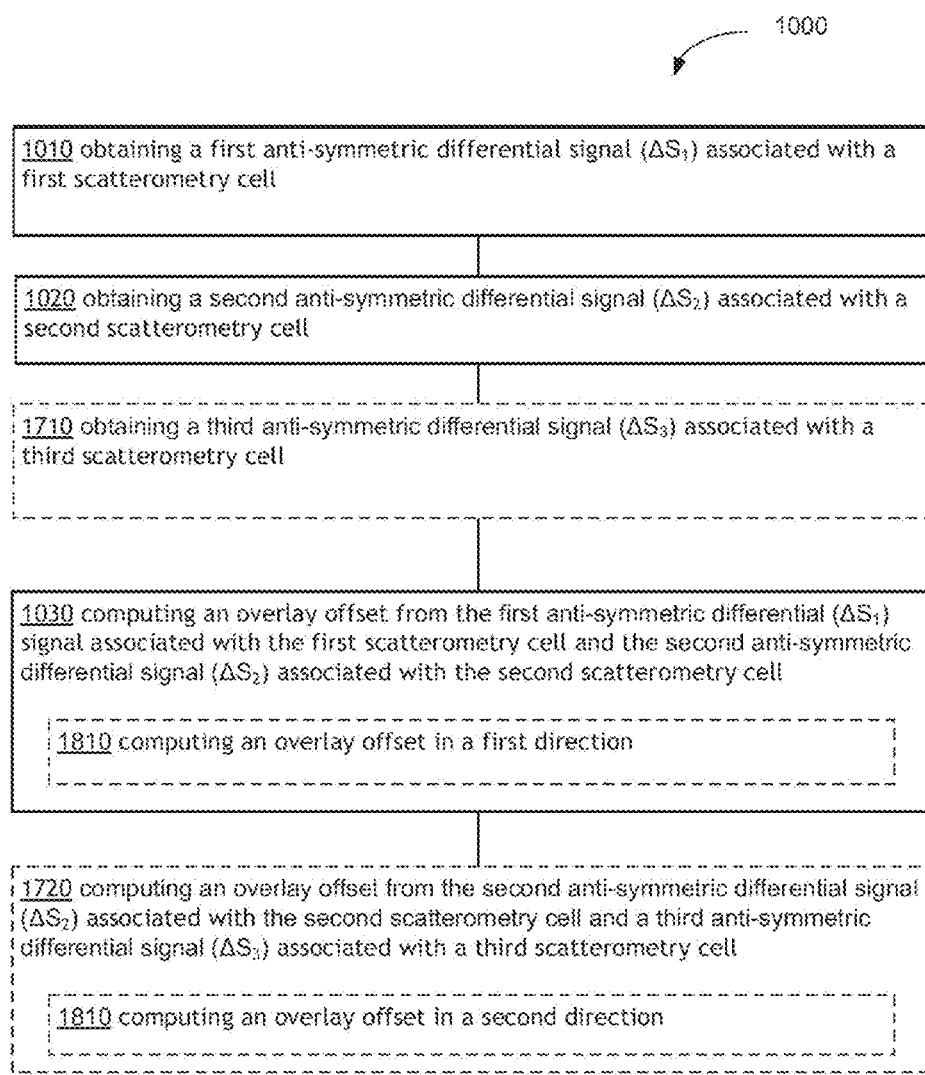

In an alternate embodiment, method 1000 may include additional operations 1710 and 1720 as shown in FIG. 17.

Operation 1710 depicts obtaining a third anti-symmetric differential signal ($\Delta S_3$) associated with a third scatterometry cell. For example, as shown in FIGS. 1-4, a light source 110 may illuminate a third scatterometry cell 127C of an overlay target 113 with a first beam of incident light 118 (e.g. a beam having a first polarization) to generate scattered light 119. A CCD detector 116 may receive the scattered light 119 and convert that light into electrical signals to be processed by a computing device 126. Further, the light source 110 may illuminate the third scatterometry cell 127C of an overlay target 113 with a second beam of incident light 118 (e.g. a beam having a second polarization) to generate scattered light 119. A CCD detector 116 may receive the scattered light 119 and convert that light into electrical signals to be processed by a computing device 126. The computing device 126 may receive the electronic signal responses associated with each illumination of the scatterometry cell 127C and compute a differential between the signals.

Operation 1720 depicts computing an overlay offset from the second anti-symmetric differential signal ($\Delta S_2$) associated with the second scatterometry cell and a third anti-symmetric differential signal ($\Delta S_3$) associated with a third scatterometry cell. For example, in the case of the second cell 127B and a third cell 127C of a overlay target 113 having programmed offsets $v_2=f_0$ and $v_3=-f_0$ in a particular direction and differential signals $\Delta S_2$ (as determined at Operation 1020) and $\Delta S_3$ (as determined at Operation 1710) which are anti-symmetric, if both the overlay and the programmed offsets are small, it may be assumed that the differential signals are linear functions of the total offsets:

$$\Delta S_2 \propto f_0 + \text{overlay}; \Delta S_3 \propto -f_0 + \text{overlay}.$$

Therefore, the overlay offset a cell pair 128B may be computed as:

$$\text{overlay} = f_0 \cdot \frac{\Delta S_2 + \Delta S_3}{\Delta S_2 - \Delta S_3}.$$

The foregoing described embodiments of the invention may be provided as illustrations and descriptions. They may be not intended to limit the invention to precise form described. For example, many of the methods described herein in the context of scatterometry apply equally to polarized reflectometry. Other variations and embodiments may be possible in light of above teachings, and it may be thus intended that the scope of invention not be limited by this Detailed Description, but rather by the appended claims.

The foregoing detailed description has set forth various embodiments of the devices and/or processes via the use of block diagrams, flowcharts and/or examples. Insofar as such block diagrams, flowcharts and/or examples contain one or more functions and/or operations, it will be understood by those within the art that each function and/or operation within such block diagrams, flowcharts or examples can be implemented, individually and/or collectively, by a wide range of hardware, software, firmware or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware may be well within the skill of one of skill in the art in light of this disclosure. In addition, those skilled in the art will appreciate that the mechanisms of the subject matter described herein may be capable of being distributed as a program product in a variety of forms, and that an illustrative embodiment of the subject matter described herein applies regardless of the particular type of signal bearing medium used to actually carry out the distribution. Examples of a signal bearing medium include, but may be not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which could be implemented, individually and/or collectively, by a wide range of hardware, software, firmware, or any combination thereof can be viewed as being composed of various types of "electrical circuitry." Consequently, as used herein "electrical circuitry" includes, but may be not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The herein described subject matter sometimes illustrates different components contained within, or connected with, different other components. It may be to be understood that such depicted architectures may be merely exemplary, and that in fact many other architectures may be implemented which achieve the same functionality. In a conceptual sense, any arrangement of components to achieve the same functionality may be effectively "associated" such that the desired functionality may be achieved. Hence, any two components herein combined to achieve a particular functionality can be seen as "associated with" each other such that the desired functionality may be achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but may be not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise. While particular aspects of the present subject matter described herein have been shown and described, it will be apparent to those skilled in the art that, based upon the teachings herein, changes and modifications may be made without departing from the subject matter described herein and its broader aspects and, therefore, the appended claims may be to encompass within their scope all such changes and modifications as may be within the true spirit and scope of the subject matter described herein. It will be understood by those within the art that, in general, terms used herein, and especially in the appended claims (e.g., bodies of the appended claims) may be generally intended as "open" terms (e.g., the term "including" should be interpreted as "including but not limited to," the term "having" should be interpreted as "having at least," the term "includes" should be interpreted as "includes but may be not limited to," etc.). It will be further understood by those within the art that if a specific number of an introduced claim recitation may be intended, such intent will be explicitly recited in the claim and in the absence of such recitation, no such intent may be present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation may be explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." may be used, in general such a construction may be intended in the sense one having skill in the art may understand the convention (e.g., "a system having at least one of A, B, and C" may include but not be limited to systems that have A alone, B alone, C alone, A and B together, A and C together, B and C together, and/or A, B, and C together, etc.). In those instances where a convention analogous to "at least one of A, B, or C, etc." may be used, in general such a construction may be intended in the sense one having skill in the art may understand the convention (e.g., "a system having at least one of A, B, or C" may include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows may be presented in a sequence(s), it should be understood that the various operations may be performed in other orders than those which may be illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives may be generally not intended to exclude such variants, unless context dictates otherwise.

Although specific dependencies have been identified in the claims, it may be to be noted that all possible combinations of the features of the claims may be envisaged in the present application, and therefore the claims may be to be interpreted to include all possible multiple dependencies. It may be believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described may be merely explanatory, and it may be the intention of the following claims to encompass and include such changes.

What is claimed:

1. A method for determining an overlay offset comprising:
    obtaining a first anti-symmetric differential signal ($\Delta S_1$) associated with a first scatterometry cell;
    obtaining a second anti-symmetric differential signal ($\Delta S_2$) associated with a second scatterometry cell; and
    computing an overlay offset from the first anti-symmetric differential ($\Delta S_1$) signal associated with the first scatterometry cell and the second anti-symmetric differential signal ($\Delta S_2$) associated with the second scatterometry cell according to the equation:

$$\text{overlay offset} = f_0 \cdot \frac{\Delta S_1 + \Delta S_2}{\Delta S_1 - \Delta S_2}$$

wherein $f_0$ is a magnitude of a programmed offset for the first scatterometry cell and the second scatterometry cell.

2. The method of claim 1,
    wherein the first scatterometry cell comprises a two-dimensional grating pattern having:
    a first programmed offset in a first direction; and
    a second non-zero programmed offset in a second direction orthogonal to the first direction, and wherein the second scatterometry cell comprises a two-dimensional grating pattern having:
a first programmed offset in the first direction unequal to the first programmed offset of the first scatterometry cell; and
a second non-zero programmed offset in the second direction equal to the second programmed offset of the first scatterometry cell.

3. The method of claim 1, further comprising:
receiving one or more scattering signals.

4. The method of claim 1, further comprising:
obtaining a third anti-symmetric differential signal ($\Delta S_3$) associated with a third scatterometry cell.

5. The method of claim 1, further comprising:
providing one or more illumination beams from a source.

6. The method of claim 4, further comprising:
computing an overlay offset from the second anti-symmetric differential signal ($\Delta S_2$) associated with the second scatterometry cell and a third anti-symmetric differential signal ($\Delta S_3$) associated with a third scatterometry cell.

7. The method of claim 6,
wherein the computing an overlay offset from the first anti-symmetric differential ($\Delta S1$) signal associated with the first scatterometry cell and the second anti-symmetric differential signal ($\Delta S2$) associated with the second scatterometry cell comprises:
computing an overlay offset in a first direction; and
wherein the computing an overlay offset from the second anti-symmetric differential signal ($\Delta S2$) associated with the second scatterometry cell and a third anti-symmetric differential signal ($\Delta S3$) associated with a third scatterometry cell comprises:
computing an overlay offset in a second direction orthogonal to the first direction.

8. The method of claim 5, wherein the providing one or more illumination beams from a source comprises:
providing one or more illumination beams from a source having an at least partially annular illumination pupil.

9. The method of claim 5, wherein the providing one or more illumination beams from a source comprises:
providing one or more illumination beams from a source having an at least partially apodized illumination pupil.

10. The method of claim 5, wherein the providing one or more illumination beams from a source comprises:
providing a monochromatic illumination beam from a source.

11. The method of claim 5, wherein the providing one or more illumination beams from a source comprises:
providing an illumination beam from a source comprising a sequence of wavelengths.

12. A method for determining an overlay offset comprising:
a) obtaining a first anti-symmetric differential signal ($\Delta S1$) associated with a first scatterometry cell, wherein the obtaining a first anti-symmetric differential signal ($\Delta S_1$) associated with a first scatterometry cell includes:
  i) obtaining scattering signals generated by a first scatterometry cell in response to illumination by a first illumination beam and scattering signals generated by the first scatterometry cell in response to illumination by a second illumination beam, wherein the obtaining scattering signals generated by a first scatterometry cell in response to illumination by a first illumination beam and scattering signals generated by the first scatterometry cell in response to illumination by a second illumination beam includes:
    1) illuminating the first scatterometry cell with an illumination beam having a first polarization;
    2) imparting a second polarization to scattering signals generated by the first scatterometry cell in response to illumination by the illumination beam having the first polarization;
    3) illuminating the first scatterometry cell with an illumination beam having the second polarization; and
    4) imparting the first polarization to scattering signals generated by the first scatterometry cell in response to illumination by an illumination beam having the second polarization; and
  ii) computing a differential signal ($\Delta S_1$) between: the scattering signals generated by the first scatterometry cell in response to illumination by the first illumination beam and the scattering signals generated by the first scatterometry cell in response to illumination by the second illumination beam; and
b) obtaining a second anti-symmetric differential signal ($\Delta S_2$) associated with a second scatterometry cell, wherein the obtaining a second anti-symmetric differential signal ($\Delta S_2$) associated with a second scatterometry cell includes:
  i) obtaining scattering signals generated by a second scatterometry cell in response illumination by a first illumination beam and scattering signals generated by the second scatterometry cell in response to illumination by a second illumination beam, wherein obtaining scattering signals generated by a second scatterometry cell in response illumination by a first illumination beam and scattering signals generated by the second scatterometry cell in response to illumination by a second illumination beam comprises:
    1) illuminating the second scatterometry cell with an illumination beam having the first polarization;
    2) imparting the second polarization to scattering signals generated by the second scatterometry cell in response to illumination by an illumination beam having the first polarization;
    3) illuminating the second scatterometry cell with an illumination beam having the second polarization; and
    4) imparting the first polarization to scattering signals generated by the second scatterometry cell in response to illumination by an illumination beam having the second polarization; and
  ii) computing a second differential signal ($\Delta S_2$) between: the scattering signals generated by the second scatterometry cell in response to illumination by the first illumination beam and the scattering signals generated by the second scatterometry cell in response to illumination by the second illumination beam;
c) imparting a phase shift to an illumination beam having at least one of the first polarization and the second polarization;
d) imparting a phase shift to scattering signals generated by at least one of the first scatterometry cell and the second scatterometry cell;
e) imparting a second phase shift to an illumination beam having at least one of the first polarization and the second polarization; and
f) imparting a second phase shift to scattering signals generated by at least one of the first scatterometry cell and the second scatterometry cell.

13. The method of claim 12, further comprising:
routing an illumination beam having at least one of the first polarization and the second polarization through at least one waveplate; and
routing one or more scattering signals through the at least one waveplate.

14. The method of claim 12, wherein the first polarization and the second polarization are orthogonal linear polarizations.

15. The method of claim 12, wherein the first polarization is an azimuthal polarization and the second polarization is a radial polarization.

16. A system for determining an overlay offset comprising:
an illumination source configured to generate at least one illumination beam;
a detector configured for:
obtaining a first anti-symmetric differential signal ($\Delta S1$) associated with a first scatterometry cell;
obtaining a second anti-symmetric differential signal ($\Delta S2$) associated with a second scatterometry cell; and
a computing device configured for computing an overlay offset from the first anti-symmetric differential ($\Delta S1$) signal associated with the first scatterometry cell and the second anti-symmetric differential signal ($\Delta S2$) associated with the second scatterometry cell according to the equation:

$$\text{overlay offset} = f_0 \cdot \frac{\Delta S_1 + \Delta S_2}{\Delta S_1 - \Delta S_2}$$

wherein $f_0$ is a magnitude of a programmed offset for the first scatterometry cell and the second scatterometry cell.

17. A system for determining an overlay offset comprising:
circuitry for obtaining a first anti-symmetric differential signal ($\Delta S1$) associated with a first scatterometry cell;
circuitry for obtaining a second anti-symmetric differential signal ($\Delta S2$) associated with a second scatterometry cell; and
circuitry for computing an overlay offset from the first anti-symmetric differential ($\Delta S1$) signal associated with the first scatterometry cell and the second anti-symmetric differential signal ($\Delta S2$) associated with the second scatterometry cell according to the equation:

$$\text{overlay offset} = f_0 \cdot \frac{\Delta S_1 + \Delta S_2}{\Delta S_1 - \Delta S_2}$$

wherein $f_0$ is a magnitude of a programmed offset for the first scatterometry cell and the second scatterometry cell.

* * * * *